(12) United States Patent
Larson et al.

(10) Patent No.: US 11,180,801 B2
(45) Date of Patent: Nov. 23, 2021

(54) DIFFERENTIAL TAGGING OF RNA FOR PREPARATION OF A CELL-FREE DNA/RNA SEQUENCING LIBRARY

(71) Applicant: GRAIL, LLC, Menlo Park, CA (US)

(72) Inventors: Matthew Larson, San Francisco, CA (US); H. John Kim, San Francisco, CA (US); Nick Eattock, Hercules, CA (US); Arash Jamshidi, Menlo Park, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

(21) Appl. No.: 16/177,105

(22) Filed: Oct. 31, 2018

(65) Prior Publication Data

US 2019/0062831 A1 Feb. 28, 2019

Related U.S. Application Data

(62) Division of application No. 15/638,220, filed on Jun. 29, 2017, now Pat. No. 10,144,962.

(60) Provisional application No. 62/368,025, filed on Jul. 28, 2016, provisional application No. 62/357,281, filed on Jun. 30, 2016.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
CPC ............................ C12Q 1/6869; C12Q 1/6806
USPC ......................................................... 506/16
See application file for complete search history.

(56) References Cited

U.S. PATENT DOCUMENTS

| | | | |
|---|---|---|---|
| 5,234,809 A | 8/1993 | Boom et al. |
| 5,476,930 A | 12/1995 | Letsinger et al. |
| 5,705,628 A | 1/1998 | Hawkins |
| 5,780,613 A | 7/1998 | Letsinger et al. |
| 6,197,557 B1 | 3/2001 | Makarov et al. |
| 6,251,639 B1 | 6/2001 | Kurn |
| 7,001,724 B1 | 2/2006 | Greenfield |
| 7,544,473 B2 | 6/2009 | Brenner |
| 7,955,794 B2 | 6/2011 | Shen et al. |
| 9,410,173 B2 | 8/2016 | Betts et al. |
| 9,970,054 B2 | 5/2018 | Otwinowski et al. |
| 10,144,962 B2 | 12/2018 | Larson et al. |
| 2009/0026082 A1 | 1/2009 | Rothberg et al. |
| 2011/0160078 A1 | 6/2011 | Fodor et al. |
| 2014/0121116 A1 | 5/2014 | Richards et al. |
| 2014/0179562 A1 | 6/2014 | Vaidyanathan et al. |
| 2015/0275267 A1 | 10/2015 | O'Neil et al. |
| 2016/0024572 A1 | 1/2016 | Shishkin et al. |
| 2016/0053253 A1* | 2/2016 | Salathia ............ C12N 15/1096 506/4 |
| 2016/0251704 A1 | 9/2016 | Talasaz et al. |
| 2016/0304954 A1 | 10/2016 | Lin et al. |
| 2016/0319345 A1 | 11/2016 | Gnerre et al. |
| 2017/0218460 A1 | 8/2017 | Talasaz |

FOREIGN PATENT DOCUMENTS

| | | | |
|---|---|---|---|
| CN | 105 297 142 A | 2/2016 |
| WO | WO 2012/038839 A2 | 3/2012 |
| WO | WO 2013/138510 A1 | 9/2013 |
| WO | WO 2013/142389 A1 | 9/2013 |
| WO | WO 2014/043133 A1 | 3/2014 |
| WO | WO 2014/113204 A1 | 7/2014 |
| WO | WO2014152155 | * 9/2014 |
| WO | WO 2014/164486 | * 10/2014 ............... C12Q 1/68 |
| WO | WO 2014/164486 A1 | 10/2014 |
| WO | WO 2014/201273 A1 | 12/2014 |
| WO | WO 2015/031689 A1 | 3/2015 |
| WO | WO 2015/089333 A1 | 6/2015 |
| WO | WO 2016/070131 A1 | 5/2016 |
| WO | WO 2017/062863 A1 | 4/2017 |
| WO | WO 2017/096322 A1 | 6/2017 |

OTHER PUBLICATIONS

Fuchs et al. (PLOS One, published May 5, 2015).*
Altschul et al., "Basic Local Alignment Search Tool," J. Mol. Biol. 215(3):403-410 (1990).
Bentley et al., "Accurate whole human genome sequencing using reversible terminator chemistry," Nature 456:53-59 (2008).
Browne, "Metal ion-catalyzed nucleic acid alkylation and fragmentation," J. Am. Chem. Soc. 124(27):7950-7962 (2002).
Casbon et al., "A method for counting PCR template molecules with application to next-generation sequencing," Nucleic Acids Res. 39(12):e81 (2011).
Chiang et al., "High-resolution mapping of copy-number alterations with massively parallel sequencing," Nat. Methods 6(1):99-103 (2009).

(Continued)

*Primary Examiner* — Robert H Havlin
(74) *Attorney, Agent, or Firm* — Greenberg Traurig, LLP

(57) ABSTRACT

In various aspects, the present disclosure provides methods, compositions, reactions mixtures, kits, and systems for sequencing both RNA and DNA from a single source sample. In some embodiments, RNA is treated so as to differentiate RNA sequences from DNA sequences derived from the same sample. In some embodiments, the RNA and DNA are cell-free polynucleotides.

20 Claims, 10 Drawing Sheets

(56) References Cited

OTHER PUBLICATIONS

Dawson et al., "Analysis of circulating tumor DNA to monitor metastatic breast cancer," N. Engl. J. Med. 368(13):1199-1209 (2013) (Epub Mar. 13, 2013).
Dey et al., "Integrated genome and transcriptome sequencing of the same cell," Nat. Biotechnol. 33(3):285-289 (2015)(Epub Jan. 19, 2015).
Duncavage et al., "Targeted next generation sequencing of clinically significant gene mutations and translocations in leukemia," Mod. Pathol. 25(6):795-804 (2012).
Glów et al., "Sequence-specific cleavage of dsRNA by Mini-III RNase," Nucleic Acids Res. 43(5):2864-2873 (2015) (Epub Jan. 29, 2015).
Harris et al., "Single-molecule DNA sequencing of a viral genome," Science 320(5872):106-109 (2008).
Heinrich et al., "Kinase mutations and imatinib response in patients with metastatic gastrointestinal stromal tumor," J. Clin. Oncol. 21(23):4342-4349 (2003).
Kinde et al., "Detection and quantification of rare mutations with massively parallel sequencing," Proc. Natl. Acad. Sci. U.S.A. 108(23):9530-9535 (2011).
Langmead et al., "Ultrafast and memory-efficient alignment of short DNA sequences to the human genome," Genome Biol. 10(3):R25 (2009) (Epub Mar. 4, 2009).
Liu et al., "Effects of target length on the hybridization efficiency and specificity of rRNA-based oligonucleotide microarrays," Appl. Environ. Microbiol. 73(1):73-82 (2007) (Epub Oct. 27, 2006).
Macaulay et al., "G&T-seq: parallel sequencing of single-cell genomes and transcriptomes," Nat. Methods 12(6):519-522 (2015) (Epub Apr. 27, 2015).
Maldonado et al., "Determinants of BRAF mutations in primary melanomas," J. Natl. Cancer Inst. 95(24):1878-1890 (2003).
Margulies et al., "Genome sequencing in microfabricated high-density picolitre reactors," Nature 437(7057):376-380 (2005) (Epub Jul. 31, 2005).
Mehlmann et al., "Optimization of fragmentation conditions for microarray analysis of viral RNA," Anal. Biochem. 347(2):316-323 (2005) (Epub Oct. 17, 2005).
Mertes et al., "Combined ultra-low input mRNA and whole-genome sequencing of human embryonic stem cells," BMC Genomics 16:925 (2015).
Pao et al., "EGF receptor gene mutations are common in lung cancers from "never smokers" and are associated with sensitivity of tumors to gefitinib and erlotinib," Proc. Natl. Acad. Sci. U.S.A. 101(36):13306-13311 (2004) (Epub Aug. 25, 2004).
Pearson and Lipman, "Improved tools for biological sequence comparison," Proc. Natl. Acad. Sci. U.S.A. 85:2444-2448 (1988).
Reuter et al., "Simul-seq: combined DNA and RNA sequencing for whole-genome and transcriptome profiling," Nat. Methods 13(11):953-958 (2016).
Samuels et al., "High frequency of mutations of the PIK3CA gene in human cancers," Science 304(5670):554 (2004) (Epub Mar. 11, 2004).
Schmitt et al., "Detection of ultra-rare mutations by next-generation sequencing," Proc. Natl. Acad. Sci. U.S.A. 109(36):14508-14513 (2012).
Soni et al., "Progress toward ultrafast DNA sequencing using solid-state nanopores," Clin. Chem. 53(11):1996-2001 (2007) (Epub Sep. 21, 2007).
Tong et al., "Diagnostic developments involving cell-free (circulating) nucleic acids," Clin. Chim. Acta 363(1-2):187-196 (2006) (Epub Aug. 26, 2005).

\* cited by examiner

DIFFERENTIAL TAGGING OF RNA FOR PREPARATION OF A CELL-FREE DNA/RNA SEQUENCING LIBRARY

CROSS-REFERENCE

This application is a divisional of co-pending U.S. application Ser. No. 15/638,220, filed Jun. 29, 2017, entitled "DIFFERENTIAL TAGGING OF RNA FOR PREPARATION OF A CELL-FREE DNA/RNA SEQUENCING LIBRARY." U.S. application Ser. No. 15/638,220 claims priority from (1) U.S. Provisional Application No. 62/368,025, filed Jul. 28, 2016; and (2) U.S. Provisional Application No. 62/357,281, filed Jun. 30, 2016. The entire disclosures of the above-referenced applications are incorporated herein by reference in their entirety.

BACKGROUND OF THE INVENTION

Analysis of nucleic acids, such as circulating cell-free nucleic acids (e.g., cell-free DNA (cfDNA) and cell-free RNA (cfRNA)), using next generation sequencing (NGS) is recognized as a valuable method for characterizing various sample types. For example, such analyses are useful as a diagnostic tool for detection and diagnosis of cancer. Current protocols for preparing a sequencing library from a cell-free nucleic acid sample (e.g., a plasma sample) typically involve isolating a single nucleic acid population, (i.e., cfDNA or cfRNA) for preparation of a sequencing library for analysis. Because only a single nucleic acid population is isolated for analysis in such protocols, precious cell-free nucleic acid material is wasted and valuable information may be lost.

SUMMARY

In view of the foregoing, there is a need for new methods of preparing a nucleic acid sequencing libraries that captures both RNA and DNA populations (e.g. cfRNA and cfDNA populations) from the same sample for sequence analysis. The present disclosure addresses this need, and provide additional benefits as well. In some embodiments, methods of the present disclosure improve the sensitivity and/or base calling accuracy of sequencing methodologies in the identification of mutations (e.g. rare sequence variants).

In one aspect, the present disclosure provides methods of distinguishing sequences of RNA and DNA in a sample. In some embodiments, the method comprises: (a) obtaining a sample comprising both RNA and DNA; (b) reverse transcribing the RNA to produce cDNA/RNA hybrid molecules; (c) degrading the RNA of the hybrid molecules to produce single-stranded cDNA; (d) preferentially joining a tag oligonucleotide comprising a tag sequence to the single-stranded cDNA in a reaction comprising a single-stranded DNA ligase to produce tagged cDNA; and (e) sequencing the DNA and the tagged cDNA; wherein the reverse transcribing, preferentially joining, and sequencing are performed in the presence of the DNA. In some embodiments, the RNA and DNA are cell-free nucleic acids. Nucleic acids (including cell-free nucleic acids) can be isolated from any of a variety of sources, such as blood, a blood fraction (e.g. serum or plasma), urine, and other bodily fluids. In some embodiments, the reverse transcribing comprises extension of primers comprising a random sequence (e.g. one or more nucleotides selected at random from a set of two or more different nucleotides at one or more positions, with each of the different nucleotides selected at one or more positions represented in a pool of oligonucleotides comprising the random sequence). In some embodiments, the reverse transcribing comprises extension of the cDNA of the hybrid along a template-switch oligonucleotide (TSO), which may comprise a universal switch primer sequence. In some embodiments, the tag oligonucleotide is joined to a 3' end of the single-stranded cDNA. In some embodiments, the tag oligonucleotide comprises a primer binding sequence. In some embodiments, the sequencing comprises amplifying the tagged cDNA to produce double-stranded tagged cDNA. In some embodiments, amplifying the tagged cDNA comprises extending a primer hybridized to the primer binding sequence. In some embodiments, the sequencing comprises joining sequencing adapters to the tagged cDNA and the DNA. In some embodiments, the tag oligonucleotide comprises a unique molecular identifier (UMI), wherein each of a plurality of tagged cDNA molecules is distinguishable from others in the plurality of tagged cDNA molecules based on the UMI (e.g. as determined by the sequence of the UMI, optionally in combination with the sequence of the cDNA). In some embodiments, the sample is blood, a blood fraction, plasma, serum, saliva, sputum, urine, semen, transvaginal fluid, cerebrospinal fluid, or stool. In some embodiments, the sample is blood or a blood fraction (e.g. serum or plasma). In some embodiments, the method further comprises using a processor to group RNA-derived sequences separately from DNA-derived sequences based on the presence or absence of the tag sequence, or a complement of the tag sequence. In some embodiments, the method further comprises identifying presence or absence of a condition of a subject (e.g. cancer) based on the RNA-derived sequences and the DNA-derived sequences. In some embodiments, the method further comprises treating the subject based on the RNA-derived sequences and the DNA-derived sequences.

In one aspect, the present disclosure provides a method of distinguishing sequences of RNA and DNA in a sample. In some embodiments, the method comprises: (a) obtaining a sample comprising both RNA and DNA; (b) joining a tag oligonucleotide comprising a tag sequence to the RNA in a reaction comprising an RNA ligase to produce tagged RNA; (c) reverse transcribing the tagged RNA to produce tagged cDNA; and (d) sequencing the DNA and the tagged cDNA; wherein the joining, reverse transcribing, and sequencing are performed in the presence of the DNA. In some embodiments, the RNA and DNA are cell-free nucleic acids. In some embodiments, the method further comprises fragmenting the RNA to produce fragmented RNA prior to joining the tag sequence. In some embodiments, the fragmented RNA have an average size within a pre-defined range (e.g. an average or median length from about 10 to about 1,000 nucleotides in length, such as between 10-800, 10-500, 50-500, 90-200, or 50-150 nucleotides; or an average or median length of less than 1500, 1000, 750, 500, 400, 300, 250, or fewer nucleotides in length). In some embodiments, fragmenting the RNA comprises subjecting the RNA and DNA to conditions that preferentially fragment the RNA. In some embodiments, fragmenting the RNA comprises sonication, chemical fragmentation, or heating. In some embodiments, the method further comprises dephosphorylating 3' ends of fragmented RNA. In some embodiments, the tag oligonucleotide is joined to a 3' end of the RNA. In some embodiments, the tag oligonucleotide comprises a primer binding sequence. In some embodiments, the reverse transcribing comprises extending a primer hybridized to the primer binding sequence. In some embodiments, the reverse transcribing comprises extension of the tagged cDNA along a template-switch oligonucleotide (TSO), which may comprise a universal switch primer sequence. In some embodiments, the sequencing comprises amplifying the tagged cDNA to produce double-stranded tagged cDNA. In some embodiments, the sequencing comprises joining sequencing adapters to the tagged cDNA and the DNA. In some embodiments, the tag oligonucleotide comprises a unique molecular identifier (UMI), wherein each of a plurality of tagged cDNA molecules is distinguishable from others in the plurality of tagged cDNA molecules based on the UMI (e.g. as determined by the sequence of the UMI, optionally in combination with the sequence of the cDNA). In some embodiments, the sample is blood, a blood fraction, plasma, serum, saliva, sputum, urine, semen, transvaginal fluid, cerebrospinal fluid, or stool. In some embodiments, the sample is blood or a blood fraction (e.g. serum or plasma). In some embodiments, the reverse transcribing comprises extension of primers comprising a random sequence. In some embodiments, the method further comprises using a processor to group RNA-derived sequences separately from DNA-derived sequences based on the presence or absence of the tag sequence, or a complement of the tag sequence. In some embodiments, the method further comprises identifying presence or absence of a condition of a subject (e.g. cancer) based on the RNA-derived sequences and the DNA-derived sequences. In some embodiments, the method further comprises treating the subject based on the RNA-derived sequences and the DNA-derived sequences.

In one aspect, the present disclosure provides a method of sequencing cell-free nucleic acids comprising DNA and RNA from a single biological sample. In some embodiments, the method comprises: (a) obtaining a sample comprising the cell-free nucleic acids; (b) reverse transcribing the RNA to produce cDNA/RNA hybrid molecules by extending a primer, wherein the primer is covalently joined to a first member of a binding pair via a cleavage site; (c) separating the cDNA from the DNA by binding the first member of the binding pair to a substrate comprising a second member of the binding pair; (d) cleaving the cleavage site; and (e) sequencing the cDNA and the DNA after the separating. In some embodiments, the reverse transcribing comprises amplifying the cDNA to produce double-stranded tagged cDNA. In some embodiments, the amplifying comprises degrading the RNA of the hybrid molecules to produce single-stranded cDNA. In some embodiments, the sequencing comprises amplifying the cDNA to produce double-stranded tagged cDNA. In some embodiments, the primer comprises a random sequence. In some embodiments, the binding pair is comprised of a first and a second moiety, wherein the first and the second moiety have a specific binding affinity for each other (e.g., the binding pair may comprise an antigen and an antibody). In some embodiments, the binding pair comprises biotin and streptavidin. In some embodiments, the first member of the binding pair is biotin, and the second member of the binding pair is streptavidin. In some embodiments, the cleavage site comprises a restriction site cleavable with a known restriction enzyme. In some embodiments, the cleavage site comprises uracil, and cleaving the cleavage site comprises exposing the cleavage site to a uracil DNA glycosylase and a DNA glycosylase-lyase endonuclease. In some embodiments, the reverse transcribing comprises extension of cDNA along a template-switch oligonucleotide (TSO), which may comprise a universal switch primer sequence. In some embodiments, the sequencing comprises joining sequencing adapters to the tagged cDNA and the DNA. In some embodiments, the sample is blood, a blood fraction, plasma, serum, saliva, sputum, urine, semen, transvaginal fluid, cerebrospinal fluid, or stool. In some embodiments, the sample is blood or a blood fraction (e.g. serum or plasma). In some embodiments, the method further comprises identifying presence or absence of a condition of a subject (e.g. cancer) based on the RNA-derived sequences and the DNA-derived sequences. In some embodiments, the method further comprises treating the subject based on the RNA-derived sequences and the DNA-derived sequences.

In one aspect, the present disclosure provides a reaction mixture for performing any of the methods described herein. The reaction mixture can comprise one or more of the various components as described herein with respect to any of the various methods. In some embodiments, the reaction mixture comprises one or more reagents for amplifying and/or sequencing nucleic acids. Non-limiting examples of reagents include oligonucleotides (e.g. primers, probes, and adapters), enzymes (e.g. polymerases, reverse transcriptases, ribonucleases, and ligases), and buffers (e.g. sodium carbonate buffer, a sodium bicarbonate buffer, a borate buffer, a Tris buffer, a MOPS buffer, a HEPES buffer).

In one aspect, the present disclosure provides a kit for performing any of the methods described herein. The kit can comprise one or more of the various components as described herein with respect to any of the various methods. In some embodiments, the kit comprises one or more reagents for amplifying and/or sequencing nucleic acids. Non-limiting examples of reagents include oligonucleotides (e.g. primers, probes, and adapters), enzymes (e.g. polymerases, reverse transcriptases, ribonucleases, and ligases), and buffers (e.g. sodium carbonate buffer, a sodium bicarbonate buffer, a borate buffer, a Tris buffer, a MOPS buffer, a HEPES buffer). Kits may further comprise instructions for the performance of one or more methods described herein with respect to any of the various aspects.

In one aspect, the present disclosure provides systems for performing methods disclosed herein, or portions thereof. In some embodiments, the system comprises various modules for carrying out one or more steps of a method. In some embodiments, the system is a computer system.

In one aspect, the present disclosure provides computer readable medium comprising instructions executable by one or more processors to perform methods disclosed herein, or portions thereof.

DETAILED DESCRIPTION

Figure 1:
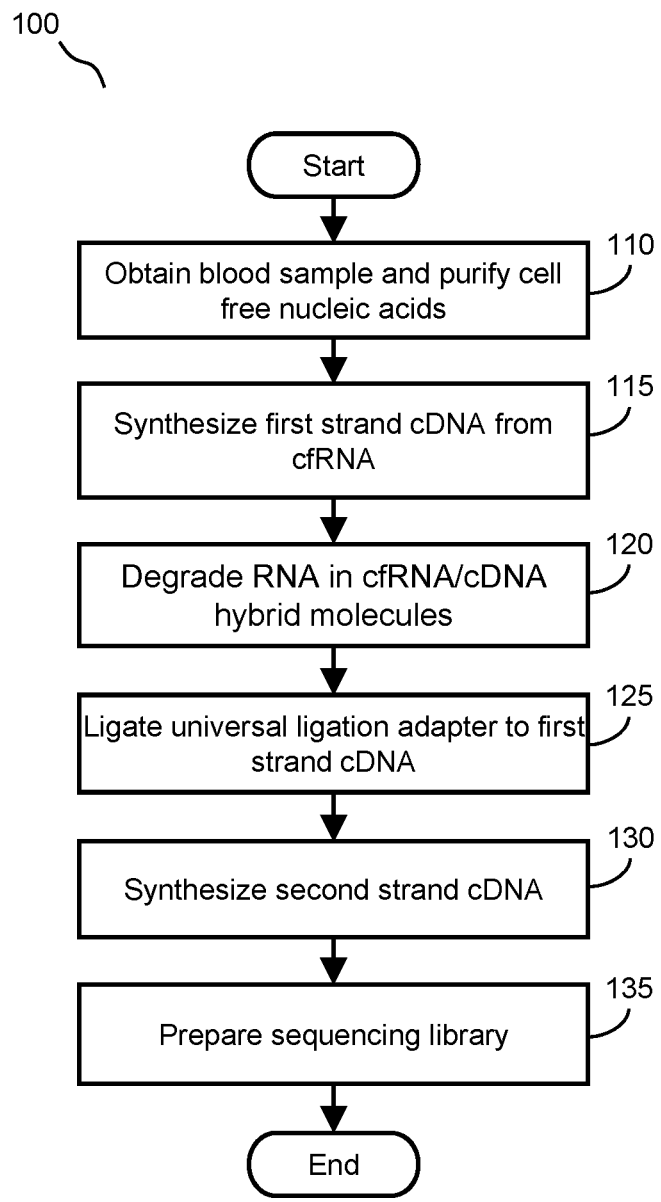
FIG. 1 illustrates a flow diagram of an example method of preparing a cell-free nucleic acid library using single strand DNA (ssDNA) ligation to tag cDNA reverse transcribed from cfRNA in a cell-free nucleic acid sample.

The practice of certain steps of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

As used in the specification and claims, the singular form "a", "an" and "the" include plural references unless the context clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleic acid," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "amplify," "amplifies," "amplified," and "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation.

In some of the various embodiments, some polynucleotides are "preferentially" treated, such as preferentially manipulating RNA in a sample comprising both RNA and DNA. In this context, "preferentially" refers to treatment that affects a greater proportion of the polynucleotide of the indicated type. In some embodiments, preferentially treating RNA indicates that of the polynucleotides affected by the treatment, at least 75%, 80%, 85%, 90%, 95%, 96%, 97%, 98%, 99%, or more of the affected polynucleotides in a reaction are RNA molecules. In some embodiments, preferentially treating RNA refers to the use of a particular treatment or reagent known in the art to have a degree of specificity for RNA over DNA. For example, reverse transcriptase is an enzyme typically used in reverse transcription reactions to transcribe RNA into cDNA, and is known to have specificity for using RNA, rather than DNA, as a template. As a further example, RNA can be preferentially treated using reagents that react with elements that are typically found in RNA and not DNA (e.g. the ribose sugar backbone, or the presence of uracil). In some embodiments, preferential treatment of RNA comprises use of enzymes that are not specific to RNA, but whose activity is preferentially directed to polynucleotides derived from RNA (e.g. cDNA) by virtue of one or more previous steps. For example, single-stranded DNA ligases may preferentially ligate oligonucleotides to cDNA in samples where cDNA is produced and rendered single-stranded in the presence of other DNA species that are predominantly double-stranded.

In general, the terms "cell-free," "circulating," and "extracellular" as applied to polynucleotides (e.g. "cell-free DNA" and "cell-free RNA") are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples.

As used herein, the terms "tag oligonucleotide" or "barcode oligonucleotide" are used interchangeably to refer to a polynucleotide comprising a sequence (the "tag" sequence or "barcode") that identifies the source of a polynucleotide comprising the tag sequence, or the complement thereof. Typically, the tag oligonucleotide comprises a defined nucleic acid sequence. However, a tag oligonucleotide need not have a defined sequence in cases where the presence of the tag is otherwise identifiable, such as when the sequence adjacent to the tag oligonucleotide is known and the tag sequence represents a deviation relative to a reference sequence at the position of the tag. Presence of the tag sequence identifies a feature of the source of the sequence comprising the tag sequence, such as a particular sample or a portion thereof, or a type of source polynucleotide. In some embodiments, presence of a tag sequence identifies a nucleic acid sequence comprising the tag sequence as originating from RNA from the sample of the subject, such as from cfRNA. In some embodiments, tag oligonucleotides comprise additional sequence elements, examples of which are described herein.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is perfectly complementary to a first sequence, or is polymerized by a polymerase using the first sequence as template, is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, or 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

As used herein, a "subject" can be a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having or potentially having a disease, disorder or condition described herein. In another embodiment, the subject is a mammal (e.g., a human) at risk of developing a disease, disorder or condition described herein.

In various aspects, the present disclosure provides methods of distinguishing sequences of RNA and DNA in a sample. In some embodiments, analyzing both RNA and DNA from a single sample provides additional information than analyzing either one alone. For example, mutations in DNA that do not affect the coding sequence (e.g. mutations in regulatory sequences, junctions indicating chromosomal rearrangements in intergenic regions, and copy number variations) would not ordinarily be detected in an analysis of RNA alone. Likewise, changes in RNA expression levels (e.g., as indicated by an increase in the proportion of one or more transcripts by comparison to a reference) and various splice variants (e.g. fusion transcripts) would not ordinarily be detected from an analysis of DNA alone. In addition, for mutations that can be detected in both DNA and RNA, analyzing both types of polynucleotides allows mutations detected in one to be confirmed by detection in the other, and/or increases the sensitivity of an assay to detect such mutations due to the increased number of polynucleotides potentially harboring them. In general, distinguishing RNA from DNA involves differential treatment of one or both with respect to the other (e.g. tagging RNA and not DNA, tagging DNA and not RNA, or tagging both DNA and RNA with different tags). In some embodiments, RNA is rendered distinguishable from DNA by way of a differential treatment of the RNA in the sample. For example, differential treatment can comprise specific incorporation of a label that facilitates physical separation of RNA from the DNA. As a further example, differential treatment can comprise association of a tag sequence specifically with RNA of a sample, or specifically with molecules derived from RNA of a sample (e.g. cDNA). In some embodiments, the differential treatment of RNA (or cDNA derived therefrom) occurs in the presence of the DNA from the sample. Various specific embodiments are described below, many of which have certain features in common. Accordingly, variations on any one specific embodiment are considered as being applicable to other embodiments, unless the context clearly indicates otherwise.

In some embodiments, the present disclosure provides a method comprising: (a) obtaining a sample comprising both RNA and DNA; (b) reverse transcribing the RNA to produce cDNA/RNA hybrid molecules; (c) degrading the RNA of the hybrid molecules to produce single-stranded cDNA; (d) preferentially joining a tag oligonucleotide comprising a tag sequence to the single-stranded cDNA in a reaction comprising a single-stranded DNA ligase to produce tagged cDNA; and (e) sequencing the DNA and the tagged cDNA; wherein the reverse transcribing, preferentially joining, and sequencing are performed in the presence of the DNA.

In some embodiments, the present disclosure provides a method comprising: (a) obtaining a sample comprising both RNA and DNA; (b) joining a tag oligonucleotide comprising a tag sequence to the RNA in a reaction comprising an RNA ligase to produce tagged RNA; (c) reverse transcribing the tagged RNA to produce tagged cDNA; and (d) sequencing the DNA and the tagged cDNA; wherein the joining, reverse transcribing, and sequencing are performed in the presence of the DNA.

Any of a variety of samples can serve as the sample comprising both RNA and DNA. In some embodiments, the sample is a biological sample. Non-limiting examples of biological samples include tissues (e.g. skin, heart, lung, kidney, bone marrow, breast, pancreas, liver, muscle, smooth muscle, bladder, gall bladder, colon, intestine, brain, prostate, esophagus, and thyroid), bodily fluids (e.g. blood, blood fractions, serum, plasma, saliva, urine, breast milk, gastric and digestive fluid, tears, semen, vaginal fluid, interstitial fluids derived from tumorous tissue, ocular fluids, sweat, mucus, oil, glandular secretions, spinal fluid, cerebral spinal fluid, placental fluid, amniotic fluid, cord blood, emphatic fluids, cavity fluids, sputum, pus), stool, swabs or washes (e.g. nasal swab, throat swab, and nasopharyngeal wash), biopsies, and other excretions or body tissues. In some embodiments, the sample is blood, a blood fraction, plasma, serum, saliva, sputum, urine, semen, transvaginal fluid, cerebrospinal fluid, or stool. In some embodiments, the sample is blood, such as whole blood or a blood fraction (e.g. serum or plasma).

In some embodiments, obtaining a sample comprising both DNA and RNA comprises extracting and/or isolating DNA and RNA from the sample. Where an extraction method is used, the method selected may depend, in part, on the type of sample to be processed. A variety of extraction methods are available. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor; (2) stationary phase adsorption methods (see e.g., U.S. Pat. No. 5,234,809); and (3) salt-induced nucleic acid precipitation methods, such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases (see, e.g., U.S. Pat. No. 7,001,724). If desired, RNase inhibitors may be added to the sample prior to, or after, extraction. For certain cell or sample types, it may be desirable to add a protein denaturation/digestion step to the protocol. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after subsequent manipulation, such as to remove excess or unwanted reagents, reactants, or products.

In some embodiments, one or more methods are employed to enrich for one or more targeted RNA species (e.g., mRNA) and/or to deplete unwanted RNA species (e.g., rRNA, tRNA, etc.) from the sample (e.g. a body fluid sample). For example, polyA tailed RNA (e.g., mRNA) molecules can be enriched for from the sample. PolyA tailed RNA can be isolated using common methods, for example by using magnetic beads functionalized with poly(T) oligonucleotides which accordingly can capture polyA RNA. Preparing a sequencing library from polyA RNA has the advantage that RNA species that do not carry a polyA tail, such as rRNA, are not recovered from the total RNA and are accordingly not carried over into the sequencing reaction. Thus, most of the sequences obtained from a sequencing library that was generated using polyA RNA corresponds to protein coding mRNA, which do carry a polyA tail. In some embodiments, total RNA in a sample is polyA tailed using known methods in the art (e.g., using terminal transferase (New England BioLabs, Ipswich, Mass.)) and purified from the sample using one or more means known in the art. In some embodiments, polyA tailed RNA species are separated based on size (e.g., using size exclusion chromatography, magnetic bead size selection (e.g., SPRIselect beads (Beckman Coulter)), or using gel electrophoresis) to isolate one RNA species (e.g. mRNA) from other RNA species (e.g. rRNA and/or tRNA). In some embodiments, total RNA is extracted using guanidinium thiocyanate-phenol-chloroform (TRIzol, Thermo Fisher Scientific), or using phenol extraction and TCA/acetone precipitation and subsequently separated using size exclusion chromatography.

In some embodiments, one or more targeted nucleic acids (e.g. rRNA) are depleted from a sample. By "depleting" a target nucleic acid, it is meant reducing the percentage of a type of undesired nucleic acid (e.g., ribosomal RNA (rRNA) or one or more particular sub-types thereof) in a sample with respect to the total nucleic acid in the sample. In some embodiments, after depletion of the target nucleic acid, the percent remaining of the target nucleic acid as compared to the initial amount of target nucleic acid in the sample is 20%, 19%, 18%, 17%, 16%, 15%, 14%, 13%, 12%, 11%, 10%, 9%, 8%, 7%, 6%, 5%, 4%, 3%, 2%, 1%, or less, including 0.5%, 0.1%, 0.01% or less. By depleting a target nucleic acid in a sample, a desired type of nucleic acid (e.g., messenger RNA (mRNA), micro RNA (miRNA), and/or any other desired type of nucleic acid) may be enriched. According to certain embodiments, in a sample in which the target nucleic acid has been depleted, a desired type of nucleic acid is enriched such that the amount of the desired type of nucleic acid relative to the total nucleic acid in the samples increases by 5% or more, such as 10% or more, 25% or more, 30% or more, 40% or more, 50% or more, 60% or more, 70% or more, including 80%, 81%, 82%, 83%, 84%, 85%, 86%, 87%, 88%, 89%, 90%, 91%, 92%, 93%, 94%, 95%, 96%, 97%, 98%, 99%, and 99.5% or more. The nucleic acid targeted for depletion can be any target nucleic acid selected by a practitioner of the subject methods. In some embodiments, the target nucleic acid is a ribonucleic acid (RNA). The RNA targeted for depletion may be any type of RNA (or sub-type thereof) including, but not limited to, a ribosomal RNA (rRNA), a microRNA (miRNA), a messenger RNA (mRNA), transfer RNA (tRNA), a small nucleolar RNA (snoRNA), a small nuclear RNA (snRNA), a long non-coding RNA (lncRNA), a non-coding RNA (ncRNA), a small interfering RNA (siRNA), a transacting small interfering RNA (ta-siRNA), a natural small interfering RNA (nat-siRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, and any combination of RNA types thereof or subtypes thereof. In general, any suitable means known in the art can be used to deplete a targeted RNA (e.g., rRNA). For example, one commercially available product is RiboZero (Illumina, San Diego, Calif.), which uses long biotinylated transcripts of rRNA as probes that hybridize to the rRNA present in the initial RNA composition. The resulting hybrids are removed with streptavidin beads. Thereby, an rRNA depleted sample is obtained. In some embodiments, rRNA is depleted using NEBNext® Ultra (New England BioLabs, Ipswich, Mass.). In some embodiments, one or more targeted nucleic acids (e.g. rRNA) are depleted using Insert Dependent Adapter Cleavage (InDAC) or AnyDeplete (NuGEN, San Carlos, Calif.). In some embodiments, one or more targeted nucleic acids (e.g. rRNA) are depleted using ZapR (Clontech, Mountain View, Calif.).

In some embodiments, the methods described herein involve manipulation of polynucleotides from a sample of a subject without cellular extraction (e.g. without a step for lysing cells, viruses, and/or other capsules comprising nucleic acids), which polynucleotides are also referred to as "cell free" polynucleotides (e.g. cell-free DNA (cfDNA), and cell-free RNA (cfRNA)). In some embodiments, DNA and RNA are manipulated directly in a biological sample as collected. In some embodiments, cell-free polynucleotides are separated from other components of a sample (e.g. cells and/or proteins) without treatment to release polynucleotides contained in cells that may be present in the sample. For samples comprising cells, the sample can be treated to separate cells from the sample. In some embodiments, a sample is subjected to centrifugation and the supernatant comprising the cell-free polynucleotides is separated for further processing (e.g. isolation of polynucleotides from other components, or other manipulation of the polynucleotides). In some embodiments, cell-free polynucleotides are purified away from other components of an initial sample (e.g. cells and/or proteins). A variety of procedures for isolation of polynucleotides without cellular extraction are available, such as by precipitation or non-specific binding to a substrate followed by washing the substrate to release bound polynucleotides.

Figure 5A:
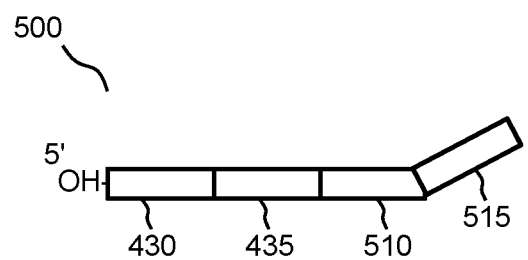
FIGS. 5A and 5B show schematic diagrams of example configurations of a universal ligation adapter and a template switch oligonucleotide, respectively, that can be used in the ligation and reverse transcription steps, such as steps illustrated in FIGS. 4A and 4B.

In some embodiments, a tag oligonucleotide is joined to RNA of the sample or to polynucleotides derived therefrom (e.g. cDNA). In some embodiments, a tag oligonucleotide is joined to DNA and RNA molecules of the sample, or to polynucleotides derived therefrom (e.g., cDNA). In some embodiments, the tag oligonucleotide is about, or at least about 10, 15, 20, 25, 30, 35, 40, 45, 50, 55, 60, 65, 70, 75, 80, 90, 100, or more nucleotides in length, or a length between any of these. In some embodiments, the tag oligonucleotide is less than about 100, 90, 80, 70, 60, 50, 40, 30, 20, 15, or fewer nucleotides in length. Tag oligonucleotides can be single-stranded or double-stranded. In some embodiments, the tag oligonucleotide is single-stranded. In general, a tag oligonucleotide comprises a tag sequence (also referred to as a "barcode") that identifies the source (or feature of the source) of a polynucleotide comprising the tag sequence, or the complement thereof. For example, presence of the tag sequence may identify the subject from whom the sample originated, a particular portion of a subdivided sample, a particular reaction from among a plurality of reactions, the type of nucleic acid in the sample from which the associated polynucleotide sequence was derived (e.g., to differentiate RNA from DNA), or a combination of any or all of these. In some embodiments, the tag sequence is about, or at least about 3, 4, 5, 6, 7, 8, 9, 10, 11, 12, 13, 14, 15, or more nucleotides in length, or a length between any of these. In some embodiments, the tag sequence is less than about 15, 14, 13, 12, 11, 10, 9, 8, 7, 6, 5, or fewer nucleotides in length. An example illustration of a tag oligonucleotide in accordance with an embodiment (referred to in some examples as a "universal ligation adapter") is illustrated in FIG. 5A.

In some cases, such as where a tag oligonucleotide is added to RNA from a sample (or its derivatives, e.g. cDNA) but not to DNA from a sample (or its derivatives, e.g. amplification products), mere presence of the tag sequence is sufficient to identify the type of nucleic acid. In such cases, the precise sequence of the sequence tag does not need to be known, and may be random or partially random (e.g. one or more nucleotides selected at random from a set of two or more different nucleotides at one or more positions, with each of the different nucleotides selected at one or more positions represented in a pool of oligonucleotides comprising the random sequence). If the tag sequence comprises a random sequence, the presence of the tag sequence can be detected by analyzing one or more additional features of the sequence with which the tag sequence is associated (e.g. sequences of additional elements that may be present in the tag oligonucleotides, fixed positions in a partially random sequence, or identifying a sequence deviation of an expected length at an expected approximate position from the end of a sequencing read in an alignment with a reference sequence).

In some embodiments, the tag sequence is a predetermined sequence. In cases where the only feature to be determined based on the presence of the tag sequence is the type of polynucleotide (e.g., where presence indicates the sequence corresponds to the sequence of an RNA from the sample), tag oligonucleotides comprising the same tag sequence can be joined to polynucleotides from multiple different samples, portions, or reactions. If two or more different samples, portions, or reactions are to be distinguished based on tag sequences, then tag sequences will preferably differ between the two or more different samples, portions, or reactions. In some embodiments, tag sequences are of sufficient length and comprise sequences that are sufficiently different to allow the identification of samples based on tag sequences with which they are associated. In some embodiments, each tag sequence in a plurality of tag sequences differs from every other tag sequence in the plurality at at least three nucleotide positions, such as at least 3, 4, 5, 6, 7, 8, 9, 10, or more nucleotide positions. A plurality of tag sequences may be represented in a pool of samples, each sample comprising polynucleotides comprising one or more tag sequences that differ from the barcodes contained in the polynucleotides derived from the other samples in the pool. In some embodiments, the methods herein further comprise identifying the sample from which a target polynucleotide is derived based on a tag sequence to which the target polynucleotide is joined. Tag sequences can also be included in other polynucleotides described herein, such as amplification primers, to facilitate multiplexed sequencing reactions with nucleic acids from multiple different samples.

In some embodiments, a tag oligonucleotide comprises one or more sequence elements in addition to the tag sequence. Non-limiting examples of additional elements include one or more amplification primer annealing sequences or complements thereof, one or more sequencing primer annealing sequences or complements thereof, one or more common sequences shared among multiple different tag oligonucleotides or subsets of different tag oligonucleotides (also referred to as "universal" sequences), one or more restriction enzyme recognition sites, one or more overhangs complementary to one or more target polynucleotide overhangs, one or more probe binding sites (e.g. for attachment to a sequencing platform, such as a flow cell for massive parallel sequencing, such as flow cells as developed by Illumina, Inc.), one or more unique molecular identifier (UMI), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence, and/or may be a common sequence present in multiple different tag oligonucleotides. Sequence elements can be located at or near the 3' end, at or near the 5' end, or in the interior of the tag oligonucleotide. In some embodiments, a sequence element is about or less than about 3, 4, 5, 6, 7, 8, 9, 10, 15, 20, 25, 30, 35, 40, 45, 50 or more nucleotides in length. In some embodiments, lengths of different sequence elements are selected independently of each other, and may or may not have the same length. In some embodiments, the tag oligonucleotide comprises 1, 2, 3, 4, 5, or more additional sequence elements.

In some embodiments, the tag oligonucleotide comprises a UMI. In general, UMIs are sequences of nucleotides applied to or identified in polynucleotides that may be used to distinguish individual nucleic acid molecules that are present in an initial reaction from one another. Since UMIs are used to distinguish different source nucleic acid molecules, they are also referred to as unique molecular identifiers. In a DNA sequencing reaction, UMIs may be sequenced along with the DNA molecules with which they are associated to determine whether the read sequences are those of one source nucleic acid molecule or another. The term "UMI" is used herein to refer to both the sequence information of a polynucleotide and the physical polynucleotide comprising that sequence information. Commonly, multiple instances of a single source molecule are sequenced. In the case of sequencing by synthesis using Ilumina's sequencing technology, the source molecule may be PCR amplified before delivery to a flow cell. Whether or not PCR amplified, the individual DNA molecules applied to flow cell may be bridge amplified or ExAmp amplified to produce a cluster. Each molecule in a cluster derives from the same source nucleic acid molecule but is separately sequenced. For error correction and other purposes, it can be helpful to determine that all reads from a single cluster are identified as deriving from the same source molecule. UMIs allow this grouping. A nucleic acid molecule that is copied by amplification or otherwise to produce multiple instances of a corresponding DNA molecule is referred to as a source nucleic acid molecule. By comparing sequences having the same UMI to one another to produce a consensus sequence, and/or by comparing overlapping sequences with different UMIs, sequencing error rates can be reduced. For example, a mutation relative to a reference sequence that is present in some, but not most or all reads with the same UMI may be ignored as not a true representation of the source nucleic acid molecule. Accuracy of calling true mutations can also be increased by requiring that any apparent mutation in a sequencing read with one UMI be observed in one or more sequencing reads with a different UMI in order to be accepted as corresponding to an actual mutation present in the source nucleic acid molecule. Accuracy can be further increased by combining approaches, such as comparing within and between UMIs, and/or between multiple different UMIs. Additional examples of UMIs and uses thereof are provided in, e.g., US20160319345, which is incorporated herein by reference.

In general, the terms "joining" and "ligation" as used herein, with respect to two polynucleotides, such as a tag oligonucleotide and a target polynucleotide (e.g. an RNA from a sample, or a corresponding cDNA), refers to the covalent attachment of two separate polynucleotides to produce a single longer polynucleotide with a contiguous backbone. A variety of methods for joining two polynucleotides are available, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, a tag oligonucleotide is joined to a target polynucleotide by a ligase, for example a DNA ligase or RNA ligase. Multiple ligases, each having characterized reaction conditions, are known in the art, and include, without limitation NAD+-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. In some embodiments, the ligase is an RNA ligase. Examples of RNA ligases include, but are not limited to T4 RNA ligase 1, T4 RNA ligase 2, TS2126 RNA ligase 1, and *Methanobacterium thermoautotrophicum* RNA ligase 1 (Mth RNA ligase). In some embodiments, ligation comprises the use of adaptase (Swift Biosciences) or Thermostable 5' AppDNA/RNA Ligase (New England BioLabs). In some embodiments, the ligation reaction preferentially joins a tag oligonucleotide to a single-stranded cDNA using a single-stranded DNA ligase. Examples of single-stranded DNA ligases include, but are not limited to TS2126 RNA ligase, T4 DNA ligase, T3 DNA ligase, and Mth RNA ligase. In some embodiments, the single-stranded DNA ligase is any DNA ligase subjected to reaction conditions that favor ligation to single-stranded cDNA. For example, cDNA can be generated in a reverse transcription reaction using a primer having a known 5' end sequence, followed by ligation between the cDNA and tag oligonucleotide in which the junction between the two is bridged by a bridge oligonucleotide comprising a first sequence that is complementary to the 5' end sequence of the primer adjacent to a second sequence that is complementary to the 3' end of the tag oligonucleotide. Thus, the bridge oligonucleotide creates a local region of double-stranded DNA at the junction of two single-stranded polynucleotides.

In some embodiments, ligation is between polynucleotides having hybridizable sequences, such as complementary overhangs. In some embodiments, ligation is between two blunt ends. In some embodiments, ligation is preferentially between tag oligonucleotides and RNA, or between tag oligonucleotides and single-stranded cDNA. Generally, a 5' phosphate is utilized in a ligation reaction. The 5' phosphate can be provided by the target polynucleotide, the tag oligonucleotide, or both (e.g., as in the case of ligation at both ends of a target polynucleotide). 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, 5' phosphates are removed prior to ligation. In some embodiments, 3' phosphates are removed prior to ligation. In some embodiments, a tag oligonucleotide is added to both ends of a target polynucleotide, wherein one or both strands at each end are joined to one or more adapter oligonucleotides. In some embodiments, separate ligation reactions are carried out for different samples using a different tag oligonucleotide comprising at least one different tag sequence for each sample, such that no tag sequence is joined to the target polynucleotides of more than one sample to be analyzed in parallel.

In some embodiments, RNA is subjected to fragmentation, such as prior to joining tag oligonucleotides to the RNA, or prior to reverse transcription. In some embodiments, the fragments have an average length, median length, or fractional distribution of lengths (e.g., accounting for at least 50%, 60%, 70%, 80%, 90%, or more) that is less than a predefined length or within a predefined range of lengths. In some embodiments, the predefined length is about or less than about 1500, 1000, 800, 600, 500, 300, 200, or 100 nucleotides in length. In some embodiments, the predefined range of lengths is a range between 10-1000, 10-800, 10-500, 50-500, 90-200, or 50-150 nucleotides in length. In some embodiments, the fragmented RNA have an average size within a pre-defined range (e.g. an average or median length from about 10 to about 1,000 nucleotides in length, such as between 10-800, 10-500, 50-500, 90-200, or 50-150 nucleotides; or an average or media length of less than 1500, 1000, 750, 500, 400, 300, 250, or fewer nucleotides in length). In some embodiments, fragmenting the RNA comprises subjecting the RNA and DNA to conditions that preferentially fragment the RNA, such as alkaline conditions in which RNA is fragmented but DNA is stable. In some embodiments, fragmenting the RNA comprises sonication, chemical fragmentation, or heating. In some embodiments, RNA species are the longest polynucleotide species in a sample, such that conditions that would be likely to fragment longer DNAs nonetheless preferentially fragment RNAs due to the higher likelihood of a fragmentation event occurring in the longer species.

A variety of fragmentation processes are available, non-limiting examples of which are provided herein. In some embodiments, the intact RNA is fragmented using basic conditions, e.g., incubation in NaOH (e.g. 50 mM NaOH) at an elevated temperature (e.g., 55° C.) for a suitable period of time (e.g., 10-30 minutes), as described in Liu et al. (Applied and Environmental Microbiology, 2007 73: 73-82). In some embodiments, the fragmentation is metal ion catalyzed in that the intact RNA is incubated with a metal ion, e.g., an ion of the lanthanide series or a divalent metal ion such as $Mg^{2+}$ or $Zn^{2+}$ (e.g., at a concentration of 5 mM to 200 mM) at an elevated temperature (e.g., in the range of 50° C. to 95° C.) for a suitable period of time (e.g., 1 minute to 1 hour), as described in, e.g. Brown et al. (J. Am. Chem. Soc. 2002 124: 7950-7962). For example, RNA may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, see above. In some embodiments, the RNA is incubated with 10 mM $ZnCl_2$ in 10 mM Tris-HCl pH 7 for 15 minutes at 70° C. to produce fragments of 60 to 200 bases in length. In some embodiments, the RNA incubated in 40 mM Tris-acetate pH 8.1, 100 mM KOAc and 30 mM MgOAc for 20-30 min at 75° C. Fragments that are generally between 38 and 150 bases in length can be obtained, as described by Mehlmann et al. (Analytical Biochemistry 2005 347: 316-323). Incubation periods and/or concentrations of reagents can be altered to increase or decrease the lengths of the fragments that are obtained, as desired.

Since fragmentation using the above methods occurs non-specifically at approximately random positions throughout the RNA, and because longer RNA molecules contain more potential sites for fragmentation to occur, the fragmentation occurs more frequently in longer RNAs on a per molecule basis. For example, fragmentation conditions that fragment RNA to fragments of 60 to 200 bases in length should, on average, fragment an RNA molecule of 3 kb in length at approximately 15 to 50 sites without much if any fragmentation of a small RNA of approximately 18-30 nucleotides in length. Fragmentation of an RNA sample that contains long RNA molecules and short polynucleotides (e.g. RNA and/or DNA molecules) therefore results in a fragmented sample that contains: a) fragments of long RNA molecules and b) short polynucleotides which are largely intact. The fragmentation may hence be carried out in the presence of oligonucleotides, which are short enough not to be fragmented during the fragmentation. Conditions can also be adjusted to produce fragments within a particular size range with no fragmentation or substantially no fragmentation (e.g. less than 20%, 10%, 5%, 1%, or less fragmentation) of polynucleotides below a particular length (e.g. less than about 500, 400, 300, 200, 100, or fewer nucleotides in length).

In some embodiments, the method further comprises dephosphorylating 3' ends of fragmented RNA. In some embodiments, the tag oligonucleotide is joined to a 3' end of the RNA.

In some embodiments, RNA is reverse transcribed in a reverse transcription (RT) reaction. In some embodiments, reverse transcription is performed before the step of joining a tag oligonucleotide, such as joining a tag oligonucleotide to a cDNA or an amplification product thereof. In some embodiments, reverse transcription is performed after the step of joining a tag oligonucleotide. In general, reverse transcription comprises extension of an oligonucleotide primer hybridized to a target RNA by an RNA-dependent DNA polymerase (also referred to as a "reverse transcriptase"), using the target RNA molecule as the template to produce a complementary DNA (cDNA). Examples of reverse transcriptases include, but are not limited to, retroviral reverse transcriptase (e.g., Moloney Murine Leukemia Virus (M-MLV), Avian Myeloblastosis Virus (AMV) or Rous Sarcoma Virus (RSV) reverse transcriptases), Superscript I™, Superscript II™, Superscript III™, retrotransposon reverse transcriptase, hepatitis B reverse transcriptase, cauliflower mosaic virus reverse transcriptase, bacterial reverse transcriptase, and mutants, variants or derivatives thereof. In some embodiments, the reverse transcriptase is a hot-start reverse transcriptase enzyme.

Oligonucleotide primers utilized in reverse transcription reactions are referred to herein as "RT primers." In some embodiments, the RT primer is about or at least about 10, 15, 20, 25, 30, 35, 40, 45, 50, 55, 60, 65, 70, 75, 80, 90, 100, or more nucleotides in length, or a length between any of these. In some embodiments, the RT primer is less than about 100, 90, 80, 70, 60, 50, 40, 30, 20, 15, or fewer nucleotides in length. In some embodiments, the RT primer is between 5-50, between 10-35, or between 15-25 nucleotides in length. An RT primer hybridizes to an RNA to be reverse transcribed via base complementarity between the RNA and a complementary sequence in the RT primer. In some embodiments, the RT reaction comprises one or more RT primers in which the complementary sequence is pre-defined, such as when a particular target (e.g. one or more genes) or a particular class of targets (e.g. mRNA, targeted via complementarity to the poly-A tails) is desired to be detected. In some embodiments, a plurality of different RT primers, each having a different pre-defined complementary sequence, are present in a single reaction, such that a plurality of corresponding RNA target molecules are reverse transcribed. For example, an RT reaction can comprise about or at least about 2, 5, 10, 15, 20, 25, 30, 40, 50, 75, 100, 150, 200, 300, 400, 500, or more different RT primers. In some embodiments, the complementary sequence comprises a random or partially random sequence (e.g. one or more nucleotides selected at random from a set of two or more different nucleotides at one or more positions, with each of the different nucleotides selected at one or more positions represented in a pool of oligonucleotides comprising the random sequence). In some embodiments, the complementary sequence of an RT primer is about, or at least about 3, 4, 5, 6, 7, 8, 9, 10, 11, 12, 13, 14, 15, or more nucleotides in length, or a length between any of these. In some embodiments, the complementary sequence is less than about 15, 14, 13, 12, 11, 10, 9, 8, 7, 6, 5, or fewer nucleotides in length. In some embodiments, the complementary sequence is a random hexamer or random nonamer.

In some embodiments, the RT primer comprises one or more sequence elements in addition to the complementary sequence. Non-limiting examples of additional elements include one or more amplification primer annealing sequences or complements thereof, one or more sequencing primer annealing sequences or complements thereof, one or more common sequences shared among multiple different RT primers or subsets of different RT primers (also referred to as "universal" sequences), one or more restriction enzyme recognition sites, one or more probe binding sites (e.g. for attachment to a sequencing platform, such as a flow cell for massive parallel sequencing, such as flow cells as developed by Illumina, Inc.), one or more unique molecular identifier (UMI), one or more random or near-random sequences, and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence, and/or may be a common sequence present in multiple different RT primers. Sequence elements can be located at or near the 3' end, at or near the 5' end, or in the interior of the RT primer. In some embodiments, a sequence element is about or less than about 3, 4, 5, 6, 7, 8, 9, 10, 15, 20, 25, 30, 35, 40, 45, 50 or more nucleotides in length. In some embodiments, lengths of different sequence elements are selected independently of each other, and may or may not have the same length. In some embodiments, the RT primer comprises 1, 2, 3, 4, 5, or more additional sequence elements. In some embodiments, the RT primer comprises one or more chemical modifications, one or more labels, or a combination of these. For example, a label can comprise a member of a binding pair that is jointed to the RT primer via a cleavage site.

In some embodiments, the RT reaction comprises a template switch oligonucleotide (TSO). In general, a TSO is an oligonucleotide that serves as a second template for the extension of a polynucleotide (e.g. a cDNA) that was first extended along a first template (e.g. an RNA template in an RT reaction). In some embodiments, the TSO replaces the first template before the extension reaction completes extension along the first template. In some embodiments, extension along the TSO proceeds after extension along the first template reaches the 5' end of the first template. In some embodiments, the TSO is about or at least about 10, 15, 20, 25, 30, 35, 40, 45, 50, 55, 60, 65, 70, 75, 80, 90, 100, or more nucleotides in length, or a length between any of these. In some embodiments, the TSO is less than about 100, 90, 80, 70, 60, 50, 40, 30, 20, 15, or fewer nucleotides in length. To serve as a second template, the TSO hybridizes to the polynucleotide to be extended via base complementarity between the polynucleotide to be extended and a complementary sequence in the TSO. In some embodiments, the TSO complementary sequence comprises a defined sequence, such as a sequence that is complementary to a defined sequence at the 3' end of polynucleotides extended along the first template (referred to as the "initial extension product" for the purposes of this example). The initial extension product may comprise a defined sequence resulting from terminal transferase activity of the polymerase involved. For example, an RT reaction can comprise a reverse transcriptase (e.g. M-MLV RT) having terminal transferase activity such that a homonucleotide stretch (e.g., a homo-trinucleotide, such as C-C-C) is added to the 3' end of the initial extension product, and the complementary sequence of the TSO includes a homonucleotide stretch (e.g., a homo-trinucleotide, such as G-G-G) complementary to that of the homonucleotide stretch added by the terminal transferase activity. As a further example, RNA species having a defined 5' end (e.g. a 5' cap structure) can be manipulated to add a defined sequence at the 5' end which can serve as a defined sequence to which a defined TSO complementary sequence hybridizes. In some embodiments, the TSO complementary sequence is a defined sequence referred to as a "universal switch primer" and is complementary to a sequence common to multiple different RNAs (e.g., a common sequence added by terminal transferase activity). In some embodiments, the TSO complementary sequence is about or less than about 3, 4, 5, 6, 7, 8, 9, 10, 15, 20, or more nucleotides in length, or a length between any of these. In some embodiments, the TSO comprises a 3' end that cannot be extended under the conditions in which it serves as the template for extension.

Figure 5B:
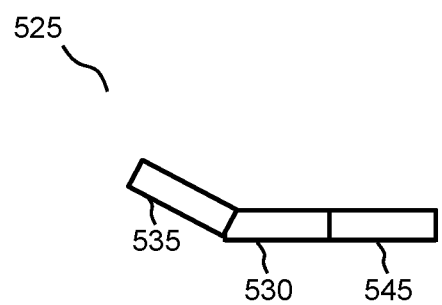

In some embodiments, the TSO comprises one or more sequence elements in addition to the complementary sequence. Non-limiting examples of additional elements include one or more amplification primer annealing sequences or complements thereof, one or more sequencing primer annealing sequences or complements thereof, one or more restriction enzyme recognition sites, one or more probe binding sites (e.g. for attachment to a sequencing platform, such as a flow cell for massive parallel sequencing, such as flow cells as developed by Illumina, Inc.), one or more unique molecular identifier (UMI), one or more random or near-random sequences, and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence, or these can be separate sequences in the TSO. Additional sequence elements in a TSO are typically located 5' relative to the complementary sequence. In some embodiments, a sequence element is about or less than about 3, 4, 5, 6, 7, 8, 9, 10, 15, 20, 25, 30, 35, 40, 45, 50 or more nucleotides in length. In some embodiments, lengths of different sequence elements are selected independently of each other, and may or may not have the same length. In some embodiments, the TSO comprises 1, 2, 3, 4, 5, or more additional sequence elements. For general examples of TSOs and reactions comprising TSOs, see e.g. U.S. Pat. No. 9,410,173. An example illustration of a TSO in accordance with an embodiment is illustrated in FIG. 5B.

The immediate product of a typical RT reaction is an RNA-DNA hybrid molecule comprising the template RNA (and optionally a TSO) hybridized to the cDNA resulting from primer extension. In some embodiments, the RNA-DNA hybrids are denatured and/or the RNA template is degraded as part of or subsequent to the RT reaction. For example, the RNA-DNA hybrids can be denatured in the presence of an enzyme that degrades RNA, such as RNase A. In some embodiments, RNA of the RNA-DNA hybrids is degraded without denaturing the complex by using an enzyme having such activity, such as RNase H. In some embodiments, the reverse transcriptase in the RT reaction comprises RNase H activity.

In some embodiments, methods provided herein comprise amplification of DNA (e.g. DNA from the sample and/or cDNA derived from RNA from the sample). In some embodiments, the amplification reaction is part of a process for preparing a sequencing library. A variety of amplification procedures are available, selection of which may depend on factors such as the type of sequencing platform to be used. Examples of amplification reactions include thermal cycling reactions and isothermal reactions. Typically, amplification reactions comprise primer extension reactions. General methods for primer-directed amplification of target polynucleotides are known in the art, and include without limitation, methods based on the polymerase chain reaction (PCR). Conditions that are generally favorable to the amplification of target sequences by PCR have been characterized, can be optimized at a variety of steps in the process, and may depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target template, and extension of the primers by a DNA polymerase. The steps can be repeated (or "cycled") in order to further amplify the target sequence. Steps in this process can be optimized for various outcomes, such as to enhance yield, decrease the formation of spurious products, and/or increase or decrease specificity of primer annealing. Example methods of optimization include, but are not limited to, adjustments to the type or amount of elements in the amplification reaction and/or to the conditions of a given step in the process, such as temperature at a particular step, duration of a particular step, and/or number of cycles. In some embodiments, an amplification reaction comprises a single primer extension step. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any suitable number of steps, such as 1, 2, 3, 4, 5, 6, 7, 8, 9, 10 or more steps. Steps can comprise any temperature or gradient of temperatures, suitable for achieving the purpose of the given step, including but not limited to, strand denaturation, primer annealing, and primer extension. Steps can be of any suitable duration, including but not limited to about, less than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted.

DNA can also be amplified isothermally. SPIA is an example of a linear, isothermal amplification method, an example description of which can be found in U.S. Pat. No. 6,251,639, which is incorporated herein by reference. Generally, the method includes hybridizing chimeric RNA/DNA amplification primers to the probes or target. The DNA portion of the probe is 3' to the RNA. Following hybridization of the primer to the template, the primer is extended with DNA polymerase. Subsequently, the RNA is cleaved from the composite primer with an enzyme that cleaves RNA from an RNA/DNA hybrid. Subsequently, an additional RNA/DNA chimeric primer is hybridized to the template such that the first extended primer is displaced from the target probe. The extension reaction is repeated, whereby multiple copies of the probe sequence are generated.

Oligonucleotide primers utilized in DNA amplification reactions are referred to herein generally as "amplification primers" or simply "primers." In some embodiments, all of the primers in an amplification reaction have the same sequence, such that there is only one type of primer participating in the reaction. In some embodiments, particularly in the case of exponential amplification, the amplification reaction comprises one or more pairs of primers, wherein in one primer of the pair hybridizes to an is extended along an initial template and the second primer hybridizes to and is extended along the complementary strand of the initial template and/or the extension product of the first primer in the pair. In some embodiments, a primer is about or at least about 10, 15, 20, 25, 30, 35, 40, 45, 50, 55, 60, 65, 70, 75, 80, 90, 100, 150, or more nucleotides in length, or a length between any of these. In some embodiments, a primer is less than about 150, 100, 90, 80, 70, 60, 50, 40, 30, 20, 15, or fewer nucleotides in length. In some embodiments, a primer is between 5-100, between 10-75, or between 15-50 nucleotides in length. A primer hybridizes to a DNA template to be amplified via base complementarity between the template DNA and a complementary sequence in the primer. In some embodiments, the amplification reaction comprises one or more primers in which the complementary sequence is pre-defined, such as when a particular target (e.g. one or more genes) or a particular class of targets (e.g. DNA and/or cDNA comprising defined sequence elements, such as sequence elements contained in a tag oligonucleotide, RT primer, TSO, or sequencing adapter) is desired to be amplified. In some embodiments, a plurality of different primers, each having a different pre-defined complementary sequence, are present in a single reaction, such that a plurality of corresponding RNA target molecules are reverse transcribed. For example, an amplification reaction can comprise about or at least about 2, 5, 10, 15, 20, 25, 30, 40, 50, 75, 100, 150, 200, 300, 400, 500, or more different primers. In some embodiments, the complementary sequence comprises a random or partially random sequence (e.g. one or more nucleotides selected at random from a set of two or more different nucleotides at one or more positions, with each of the different nucleotides selected at one or more positions represented in a pool of oligonucleotides comprising the random sequence). In some embodiments, the complementary sequence of a primer is about, or at least about 3, 4, 5, 6, 7, 8, 9, 10, 11, 12, 13, 14, 15, 20, 25 or more nucleotides in length, or a length between any of these. In some embodiments, the complementary sequence is less than about 20, 15, 14, 13, 12, 11, 10, 9, 8, 7, 6, 5, or fewer nucleotides in length. In some embodiments, the complementary sequence is complementary to a sequence element present in the template to be amplified by virtue of being joined to a tag oligonucleotide and/or an RT primer, such as a primer annealing sequence.

In some embodiments, an amplification primer comprises one or more sequence elements in addition to the complementary sequence. Non-limiting examples of additional elements include annealing sequences for one or more further amplification primers or complements thereof, one or more sequencing primer annealing sequences or complements thereof, one or more common sequences shared among multiple different RT primers or subsets of different primers (also referred to as "universal" sequences), one or more restriction enzyme recognition sites, one or more probe binding sites (e.g. for attachment to a sequencing platform, such as a flow cell for massive parallel sequencing, such as flow cells as developed by Illumina, Inc.), one or more unique molecular identifier (UMI), one or more random or near-random sequences, and combinations thereof. Two or more sequence elements can be non-adjacent to one another (e.g. separated by one or more nucleotides), adjacent to one another, partially overlapping, or completely overlapping. For example, an annealing sequence for a further amplification primer can also serve as a sequencing primer annealing sequence, and/or may be a common sequence present in multiple different primers. Sequence elements can be located at or near the 3' end, at or near the 5' end, or in the interior of the primer. In some embodiments, a sequence element is about or less than about 3, 4, 5, 6, 7, 8, 9, 10, 15, 20, 25, 30, 35, 40, 45, 50 or more nucleotides in length. In some embodiments, lengths of different sequence elements are selected independently of each other, and may or may not have the same length. Typically, DNA resulting from a DNA amplification reaction, whether single- or double-stranded prior to the reaction, is double-stranded after the reaction, unless the double-stranded amplification products are subsequently denatured.

In some embodiments, DNA from the sample, cDNA derived from RNA from the sample, and/or amplification products of any of these are sequenced to produced sequencing reads identifying the order of nucleotides present in the sequenced polynucleotides or the complements thereof. A variety of suitable sequencing techniques are available. In some embodiments, sequencing comprises massively parallel sequencing of about, or at least about 10000, 100000, 500000, 1000000, or more DNA molecules using a high-throughput sequencing by synthesis process, such as Illumina's sequencing-by-synthesis and reversible terminator-based sequencing chemistry (e.g. as described in Bentley et al., Nature 6:53-59 (2009)). In some embodiments, particularly when cfDNA is included among the polynucleotides to be sequenced, DNA is not fragmented prior to sequencing. Typically, Illumina's sequencing process comprises attachment of template DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA. This addition prepares the DNA for ligation to oligonucleotide adapters, which optionally have an overhang of a single T base at their 3' end to increase ligation efficiency. The adapter oligonucleotides are complementary to the flow-cell anchor oligos. Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the template DNA is amplified using PCR before it is subjected to cluster amplification, such as in a process described above. In some applications, the templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome, and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Another non-limiting example sequencing process is the single molecule sequencing technology of the Helicos True Single Molecule Sequencing (tSMS) technology (e.g. as described in Harris T. D. et al., Science 320:106-109 (2008)). In a typical tSMS process, a DNA sample is cleaved into, or otherwise provided as strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In some embodiments, the templates are at a density of about 100 million templates/$cm^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries.

Another illustrative, but non-limiting example sequencing process is pyrosequencing, such as in the 454 sequencing platform (Roche) (e.g. as described in Margulies, M. et al. Nature 437:376-380 (2005)). 454 sequencing typically involves two steps. In the first step, DNA is sheared into fragments of, or otherwise provided (e.g. as naturally occurring cfDNA molecules, or cDNA from naturally short RNA molecules) as DNA having sizes of approximately 300-800 base pairs, and the polynucleotides are blunt-ended. Oligonucleotide adapters are then ligated to the ends of the DNA. The adapters serve as primers for amplification and sequencing of the DNA. The DNA can be attached to capture beads, e.g., streptavidin-coated beads using, e.g., adapter B, which contains 5'-biotin tag. The DNA attached to the beads are PCR amplified within droplets of an oil-water emulsion. The result is multiple copies of clonally amplified DNA molecules on each bead. In the second step, the beads are captured in wells (e.g., picoliter-sized wells). Pyrosequencing is performed on each DNA molecule in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

Further high-throughput sequencing processes are available. Non-limiting examples include sequencing by ligation technologies (e.g., SOLiD™ sequencing of Applied Biosystems), single-molecule real-time sequencing (e.g., Pacific Biosciences sequencing platforms utilizing zero-mode wave detectors), nanopore sequencing (e.g. as described in Soni G V and Meller A. Clin Chem 53: 1996-2001 (2007)), sequencing using a chemical-sensitive field effect transistor (e.g., as described in U.S. Patent Application Publication No. 20090026082), sequencing platforms by Ion Torrent (pairing semiconductor technology with sequencing chemistry to directly translate chemically encoded information (A, C, G, T) into digital information (0, 1) on a semiconductor chip), and sequencing by hybridization. Additional illustrative details regarding sequencing technologies can be found in, e.g., U.S. Patent Application Publication No. 2016/0319345, incorporated herein by reference.

In some embodiments using UMIs, multiple sequence reads having the same UMI(s) are collapsed to obtain one or more consensus sequences, which are then used to determine the sequence of a source DNA or cDNA molecule. Multiple distinct reads may be generated from distinct instances of the same source DNA molecule, and these reads may be compared to produce a consensus sequence. The instances may be generated by amplifying a source DNA molecule prior to sequencing, such that distinct sequencing operations are performed on distinct amplification products, each sharing the source DNA molecule's sequence. Of course, amplification may introduce errors such that the sequences of the distinct amplification products have differences. In the context some sequencing technologies such as an embodiment of Illumina's sequencing-by-synthesis, a source DNA molecule or an amplification product thereof forms a cluster of DNA molecules linked to a region of a flow cell. The molecules of the cluster collectively provide a read. Typically, at least two reads are required to provide a consensus sequence. Sequencing depths of 100, 1000, and 10,000 are examples of sequencing depths useful in the disclosed embodiments for creating consensus reads for low allele frequencies (e.g., about 1% or less). In some embodiments, nucleotides that are consistent across 100% of the reads sharing a UMI or combination of UMIs are included in the consensus sequence. In some embodiments, consensus criterion can be lower than 100%. For instance, a 90% consensus criterion may be used, which means that base pairs that exist in 90% or more of the reads in the group are included in the consensus sequence. In some embodiments, the consensus criterion may be set at about, or more than about 30%, about 40%, about 50%, about 60%, about 70%, about 80%, about 90%, about 95%, or about 100%.

In some embodiments, sequencing reads (or consensus sequences thereof) are identified as originating from an RNA molecule in the source sample if the tag sequence (or the complement thereof) forms part of the sequence read (optionally, at an expected position, and/or adjacent to other expected sequence element(s)), and otherwise is identified as originating from a DNA molecule in the source sample if the tag sequence (or the complement thereof) is absent. In this way, RNA sequencing reads and DNA sequencing reads can be produced in a single sequencing reaction, but analyzed separately, and optionally compared to one another. In some embodiments, a processor is used to group RNA-derived sequences separately from DNA-derived sequences. For example, in some embodiments, a mutation relative to an internal reference (e.g. overlapping reads) or an external reference (e.g. a reference genome) is only designated as accurately representing the original molecule (e.g. a DNA molecule of the sample) if the same mutation is identified in one or more reads corresponding to an original molecule of the other type (e.g. an RNA molecule of the sample). This is particularly helpful for increasing sequencing accuracy in cases where no UMIs are used, and can further increase sequencing accuracy when used in combination with UMIs. In some embodiments, for the purposes of alignment among sequencing reads and/or between sequencing reads and a reference sequence, one or more sequences corresponding to features known not to be present in the source polynucleotides (e.g. sequences known to originate from tag oligonucleotides, RT primers, TSOs, or amplification primers) are computationally ignored (e.g. filtered out of the reads prior to alignment).

In some embodiments, sequencing reads (or consensus sequence thereof) are localized (mapped) by aligning the reads to a known reference genome. In some embodiments, localization is realized by k-mer sharing and read-read alignment. In some embodiments, the reference genome sequence is the NCBI36/hg18 sequence, which is available on the World Wide Web at genome.ucsc.edu/cgi-bin/hgGateway?org=Human&db=hg18&hgsid=166260105). In some embodiments, the reference genome sequence is the GRCh37/hg19 or GRCh38, which is available on the World Wide Web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In some embodiments, one end of clonally expanded copies of plasma polynucleotide molecules (or amplification products thereof) is sequenced and processed by bioinformatics alignment analysis for the Illumina Genome Analyzer, which uses the Efficient Large-Scale Alignment of Nucleotide Databases (ELAND) software. By aligning reads to a reference genome, the genomic locations of mutations relative to the reference sequence can be identified. In some cases, alignment will facilitate inferring an effect of the mutation and/or a property of the cell from which it originated. For example, if the mutation creates a premature stop codon in a tumor suppressor gene, it may be inferred that the source polynucleotide originated from a cancer cell, particularly if there are a statistically significant number of cancer-associated markers are detected in the sequencing reads.

In one aspect, the present disclosure provides a method of sequencing cell-free nucleic acids comprising DNA and RNA from a single biological sample. In some embodiments, the method comprises: (a) obtaining a sample comprising the cell-free nucleic acids; (b) reverse transcribing the RNA to produce cDNA/RNA hybrid molecules by extending a primer, wherein the primer is covalently joined to a first member of a binding pair via a cleavage site; (c) separating the cDNA from the DNA by binding the first member of the binding pair to a substrate comprising a second member of the binding pair; (d) cleaving the cleavage site; and (e) sequencing the cDNA and the DNA after the separating. The method differs from aspects relating to distinguishing RNA-derived from DNA-derived sequences in a single sequencing reaction in that the RNA-derived species (the cDNAs) are physically separated from DNA molecules originating from the sample prior to the sequencing. However, these different aspects can be similar in other respects. For example, disclosure relating to other aspects of the disclosure with respect to sample sources, polynucleotide sources (e.g. cell-free polynucleotides), extraction methods, methods for isolating or otherwise manipulating cell-free polynucleotides, tag oligonucleotides, UMIs, methods and compositions for joining polynucleotides, fragmentation, reverse transcription, RT primers, TSOs, amplification of DNA and cDNA, amplification primers, sequencing methods, and methods for analyzing sequencing reads is applicable here as well, with regard to various embodiments of this aspect of the disclosure. In some embodiments, separation of the cDNA from the DNA is performed prior to reverse transcription. In some embodiments, separation of cDNA from the DNA is performed after reverse transcription.

In some embodiments, DNA and cDNA are treated separately all the way through sequencing. In some embodiments, the cDNA and DNA are treated differently following separation in such a way that they can be mixed back together at some point prior to sequencing but still distinguish the sequencing reads as originating from cDNA or sample DNA. For example, after separation, a tag oligonucleotide can be joined to the cDNA or the DNA, or different tag oligonucleotides added to both, such that the tag oligonucleotides (and the tag sequences in particular) can be used as described above to distinguish RNA-derived sequences from DNA-derived sequences.

A variety of binding pairs can be utilized for the purpose of separating cDNA from sample-originating DNA. In general, a binding pair is comprised of a first and a second moiety, wherein the first and the second moiety have a specific binding affinity for each other. Suitable binding pairs include, but are not limited to, antigens/antibodies (for example, digoxigenin/anti-digoxigenin, dinitrophenyl (DNP)/anti-DNP, dansyl-X/anti-dansyl, fluorescein/anti-fluorescein, lucifer yellow/anti-lucifer yellow, and rhodamine/anti-rhodamine); biotin/avidin (or biotin/streptavidin); calmodulin binding protein (CBP)/calmodulin; hormone/hormone receptor; lectin/carbohydrate; peptide/cell membrane receptor; protein A/protein A antibody; hapten/antihapten; enzyme/cofactor; and enzyme/substrate. To facilitate physical separation of cDNA comprising a first member of a binding pair, the second member of the binding pair is typically attached (e.g., by a covalent bond) to a substrate. Possible substrates include, but are not limited to, glass, modified or functionalized glass, plastics (including acrylics, polystyrene, copolymers of styrene and other materials, polypropylene, polyethylene, polybutylene, polyurethanes, Teflon™, etc.), polysaccharides, nylon, nitrocellulose, ceramics, resins, silica, silica-based materials (e.g., silicon and modified silicon), carbon, metals, inorganic glasses, plastics, optical fiber bundles, and a variety of other polymers. In some embodiments, the substrate is in the form of a bead or other small, discrete particle, which is optionally magnetic or paramagnetic to facilitate isolation through application of a magnetic field.

The process by which the cleavage site is cleaved will depend on the nature of the cleavage site. In some embodiments, the cleavage site comprises a restriction site cleavable with a known restriction enzyme. In some embodiments, the cleavage site comprises a uracil nucleotide, in which case the strand can be cleaved at the uracil base using the enzyme uracil DNA glycosylase (UDG), which removes the nucleotide base, and endonuclease VIII to excises the abasic nucleotide. This enzyme combination is available as USER™ from New England Biolabs (NEB part number M5505). Another example of a cleavage site is an 8-oxoguanine nucleotide, which is then cleavable by the enzyme FPG (NEB part number M0240, also known as 8-oxoguanine DNA glycosylase). In some embodiments, the cleavage site is a chemical modification, for example with a disulfide or diol modification, that allows chemical cleavage at the cleavage site. In some embodiments, the cleavage site is an RNA base that is a cleavage substrate for an RNase H enzyme. In some embodiments, RNA-DNA hybrid molecules are treated to degrade the RNA component, such by denaturation and degradation, or degradation by an enzyme that specifically degrades RNA in an RNA-DNA hybrid (e.g. RNase H), examples of which are described herein, such as with regard to other aspects of the disclosure.

Any of the various aspects described herein relating to obtaining sequencing information from both DNA and RNA of a sample, whether by distinguishing RNA-derived sequences from DNA-derived sequences, separating DNA from cDNA, or some combination of the two, provide valuable sequencing information that can be used to determine one or more characteristics of the sample from which the polynucleotides were derived. Analyzing both DNA and RNA increases the sensitivity of the assay for detecting rare mutations. In some embodiments, a rare mutation detected by a method described herein is a sequence variant that is represented among the polynucleotides in the original sample at a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some embodiments, the sequence variant occurs with a frequency of about or less than about 0.1%. In some embodiments, the sequence variant occurs with a frequency of less than about 0.05%. A mutation, or sequence variant, can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, increased sensitivity for detecting sequence variants facilitates identification of a sample source (e.g., from where an environmental sample originated), presence of a contaminant (e.g., microbial contamination in a food or water sample), or presence of a genetic variant associated with the presence or absence of a condition (e.g., a disease condition, such as cancer). In some embodiments, similar detection determinations are facilitated by combining different types of information from the RNA-derived sequences and the DNA-derived sequences. For example, the combination of (1) a particular gene expression level that statistically significantly deviates from a reference expression level, and (2) a chromosomal rearrangement near the gene whose expression is affected may increase the likelihood that the source subject is affected by a particular condition, as compared to either of these pieces of information alone. Thus, information derived from analyzing sequences from both DNA and RNA of a sample includes, but is not limited to, identifying sequence variants.

In some embodiments, methods of the present disclosure, in any of the various aspects, comprise identifying the presence or absence of a condition of a subject based on the RNA-derived sequences and the DNA-derived sequences. In general, identification of a condition of a subject is said to be "based on" the RNA-derived sequences and the DNA-derived sequences if both of these sequencing results are used in making the identification. For example, a mutation in an RNA-derived sequence is used to validate a mutation in a DNA-derived sequence, and the presence of that mutation indicates the presence of a condition. As noted above, considerations other than mutations can also be utilized (e.g. in combination with one another, or in combination with identification of a mutation). Non-limiting examples of non-mutation considerations include expression levels, and epigenetic modifications. Accordingly, any of a variety of conditions having a genetic component (and not necessarily the result of mutation) can be identified by methods of the present disclosure.

In some embodiments, a mutation detected by a method of the present disclosure is a sequence variant that is correlated with a disease. In general, sequence variants for which there is statistical, biological, and/or functional evidence of association with a disease or trait are referred to as "causal genetic variants." A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Examples of diseases and gene targets with which a causal genetic variant may be associated include, but are not limited to, 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, one or more other types of cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation Ib, Congenital Finnish Nephrosis, Crohn's Disease, Cystinosis, DFNA 9 (COCH), Diabetes and Hearing Loss, Early-Onset Primary Dystonia (DYTI), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type 1b, Glycogen Storage Disease Type II, Glycogen Storage Disease Type III, Glycogen Storage Disease Type V, Gracile Syndrome, HFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-related pituitary hormome deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis, and Zellweger Syndrome Spectrum.

In some embodiments, one or more sequence variants are identified in all or part of the PIK3CA gene. Somatic mutations in PIK3CA have been frequently found in various types of cancers, for example, in 10-30% of colorectal cancers (see e.g. Samuels et al. 2004 Science. 2004 Apr. 23;

304(5670):554.). These mutations are most commonly located within two "hotspot" areas within exon 9 (the helical domain) and exon 20 (the kinase domain), which may be specifically targeted for amplification and/or analysis for the detection sequence variants. Position 3140 may also be specifically targeted.

In some embodiments, one or more sequence variants are identified in all or part of the BRAF gene. Near 50% of all malignant melanomas have been reported as harboring somatic mutations in BRAF (see e.g. Maldonado et al., J Natl Cancer Inst. 2003 Dec. 17; 95(24):1878-90). BRAF mutations are found in all melanoma subtypes but are most frequent in melanomas derived from skin without chronic sun-induced damage. Among the most common BRAF mutations in melanoma are missense mutations V600E, which substitutes valine at position 600 with glutamine. BRAF V600E mutations are associated with clinical benefit of BRAF inhibitor therapy. Detection of BRAF mutation can be used in melanoma treatment selection and studies of the resistance to the targeted therapy.

In some embodiments, one or more sequence variants are identified in all or part of the EGFR gene. EGFR mutations are frequently associated with Non-Small Cell Lung Cancer (about 10% in the US and 35% in East Asia; see e.g. Pao et al., Proc Natl Acad Sci USA. 2004 Sep. 7; 101(36):13306-11). These mutations typically occur within EGFR exons 18-21, and are usually heterozygous. Approximately 90% of these mutations are exon 19 deletions or exon 21 L858R point mutations.

In some embodiments, one or more sequence variants are identified in all or part of the KIT gene. Nearly 85% of Gastrointestinal Stromal Tumor (GIST) have been reported as harboring KIT mutations (see e.g. Heinrich et al. 2003 J Clin Oncol. 2003 Dec. 1; 21 (23):4342-9). The majority of KIT mutations are found in juxtamembrane domain (exon 11, 70%), extracellular dimerization motif (exon 9, 10-15%), tyrosine kinase 1 (TK1) domain (exon 13, 1-3%), and tyrosine kinase 2 (TK2) domain and activation loop (exon 17, 1-3%). Secondary KIT mutations are commonly identified after target therapy imatinib and after patients have developed resistance to the therapy.

Additional non-limiting examples of genes associated with cancer, all or a portion of which may be analyzed for sequence variants, and/or other features of DNA and RNA derived from such cancer cells, according to methods described herein include, but are not limited to PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR; (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; and Apc. Further examples are provided elsewhere herein.

In some embodiments, a cancer is diagnosed based on the RNA-derived sequences and DNA-derived sequences. Examples of cancers include, but are not limited to, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof. Additional examples of cancers and other conditions, and mutations with which the conditions are associated are described in, e.g., U.S. Patent Application Publication No. 2016/0304954 (see e.g., Tables 4-6), which is incorporated herein by reference.

In some embodiments, one or more causal genetic variants are sequence variants associated with a particular type or stage of cancer, or of cancer having a particular characteristic (e.g. metastatic potential, drug resistance, drug responsiveness). In some embodiments, the disclosure provides methods for the determination of prognosis, such as where certain mutations or other genetic characteristics are known to be associated with patient outcomes. For example, circulating tumor DNA (ctDNA) has been shown to be a better biomarker for breast cancer prognosis than the traditional cancer antigen 53 (CA-53) and enumeration of circulating tumor cells (see e.g. Dawson, et al., N Engl J Med 368:1199 (2013)).

In some embodiments, methods of the present disclosure comprise treating a subject based on the RNA-derived and DNA-derived sequences detected in a sample from the subject. By way of non-limiting example, methods disclosed herein can be used in making therapeutic decisions, guidance and monitoring, as well as development and clinical trials of cancer therapies. For example, treatment efficacy can be monitored by comparing patient DNA and RNA in samples from before, during, and after treatment with particular therapies such as molecular targeted therapies (monoclonal drugs), chemotherapeutic drugs, radiation protocols, etc. or combinations of these. In some embodiments, cell-free polynucleotides are monitored to see if certain mutations, expression levels, or other features of DNA or RNA increase or decrease, or new mutations appear, after treatment, which can allow a physician to alter a treatment (continue, stop or change treatment, for example) in a much shorter period of time than afforded by methods of monitoring that track traditional patient symptoms. In some embodiments, a method further comprises the step of diagnosing a subject based on the RNA-derived sequences and DNA-derived sequences, such as diagnosing the subject with a particular stage or type of cancer associated with a detected sequence variant, or reporting a likelihood that the patient has or will develop such cancer.

In one aspect, the present disclosure provides compositions for use in or produced by methods described herein, including with respect to any of the various other aspects of this disclosure. Compositions of the disclosure can comprise any one or more of the elements described herein. In some embodiments, compositions include one or more of the following: one or more solid supports comprising oligonucleotides attached thereto, one or more oligonucleotides for attachment to a solid support, one or more tag oligonucleotides, one or more RT primers, one or more TSOs, one or more amplification primers, one or more oligonucleotide primers comprising a first member of a binding pair, one or more sequencing adapters, one or more solid surfaces (e.g. beads) comprising a second member of a binding pair, one or more sequencing primers, one or more enzymes (e.g. one or more of a polymerase, a reverse transcriptase, a ligase, a ribonuclease, and a glycosylase), one or more buffers (e.g. sodium carbonate buffer, a sodium bicarbonate buffer, a borate buffer, a Tris buffer, a MOPS buffer, a HEPES buffer), reagents for utilizing any of these, reaction mixtures comprising any of these, and instructions for using any of these.

In one aspect, the present disclosure provides reaction mixtures for use in or produced by methods described herein, including with respect to any of the various other aspects of this disclosure. In some embodiments, the reaction mixture comprises one or more compositions described herein.

In one aspect, the present disclosure provides kits for use in any of the methods described herein, including with respect to any of the various other aspects of this disclosure. In some embodiments, the kit comprises one or more compositions described herein. Elements of the kit can further be provided, without limitation, in any amount and/or combination (such as in the same kit or same container). In some embodiments, kits comprise additional agents for use according to the methods of the invention. Kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

In one aspect, the present disclosure provides systems, such as computer systems, for implementing methods described herein, including with respect to any of the various other aspects of this disclosure. It should be understood that it is not practical, or even possible in most cases, for an unaided human being to perform computational operations involved in some embodiments of methods disclosed herein. For example, mapping a single 30 bp read from a sample to any one of the human chromosomes might require years of effort without the assistance of a computational apparatus. Of course, the challenge of unaided sequence analysis and alignment is compounded in cases where reliable calls of low allele frequency mutations require mapping thousands (e.g., at least about 10,000) or even millions of reads to one or more chromosomes. Accordingly, some embodiments of methods described herein are not capable of being performed in the human mind alone, or with mere pencil in paper, but rather necessitate the use of a computational system, such as a system comprising one or more processors programmed to implement one or more analytical processes.

In some embodiments, the disclosure provides tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In some embodiments, the data or information employed in methods and systems disclosed herein are provided in an electronic format. Examples of such data or information include, but are not limited to, sequencing reads derived from a nucleic acid sample, reference sequences (including reference sequences providing solely or primarily polymorphisms), sequences of one or more oligonucleotides used in the preparation of the sequencing reads (including portions thereof, and/or complements thereof), calls such as cancer diagnosis calls, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In some embodiments, provided herein is a computer program product for generating an output indicating the sequences of DNA and RNA in a test sample. The computer product may contain instructions for performing any one or more of the above-described methods for determining DNA and RNA sequences. As explained, the computer product may include a non-transitory and/or tangible computer readable medium having a computer executable or compilable logic (e.g., instructions) recorded thereon for enabling a processor to determine a sequence of interest. In one example, the computer product includes a computer readable medium having a computer executable or compilable logic (e.g., instructions) recorded thereon for enabling a processor to diagnose a condition and/or determine a nucleic acid sequence of interest.

In some embodiments, methods described herein (or portions thereof) are performed using a computer processing system which is adapted or configured to perform a method for determining the sequence of polynucleotides derived from DNA and RNA of a sample, such as one or more sequences of interest (e.g. an expressed gene or portion thereof). In some embodiments, a computer processing system is adapted or configured to perform a method as described herein. In one embodiment, the system includes a sequencing device adapted or configured for sequencing polynucleotides to obtain the type of sequence information described elsewhere herein, such as with regard to any of the various aspects described herein. In some embodiments, the apparatus includes components for processing the sample, such as liquid handlers and sequencing systems, comprising modules for implementing one or more steps of any of the various methods described herein (e.g. sample processing, polynucleotide purification, and various reactions (e.g. RT reactions, amplification reactions, and sequencing reactions).

In some embodiments, sequence or other data is input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store read counts for various chromosomes or genomes, etc. The memory may also store various routines and/or programs for analyzing the sequence or mapped data. In some embodiments, the programs/routines include programs for performing statistical analyses.

In one example, a user provides a polynucleotide sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet, which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods comprise collecting data regarding a plurality of polynucleotide sequences (e.g., reads, consensus sequences, and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data.

Among the types of electronically formatted data that may be stored, transmitted, analyzed, and/or manipulated in systems, apparatus, and methods disclosed herein are the following: reads obtained by sequencing nucleic acids, consensus sequences based on the reads, the reference genome or sequence, thresholds for calling a test sample as either affected, non-affected, or no call, the actual calls of medical conditions related to the sequence of interest, diagnoses (clinical condition associated with the calls), recommendations for further tests derived from the calls and/or diagnoses, treatment and/or monitoring plans derived from the calls and/or diagnoses. In some embodiments, these various types of data are obtained, stored transmitted, analyzed, and/or manipulated at one or more locations using distinct apparatus. The processing options span a wide spectrum of options. At one end of the spectrum, all or much of this information is stored and used at the location where the test sample is processed, e.g., a doctor's office or other clinical setting. At the other end of the spectrum, the sample is obtained at one location, it is processed and optionally sequenced at a different location, reads are aligned and calls are made at one or more different locations, and diagnoses, recommendations, and/or plans are prepared at still another location (which may be a location where the sample was obtained).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

FIG. 1 illustrates a flow diagram of an example of a method 100 of preparing a cell-free nucleic acid library using single strand DNA ligation to tag cDNA reverse transcribed from cfRNA in a cell-free nucleic acid sample. Method 100 includes, but is not limited to, the following steps.

In a step 110, a blood sample is obtained and circulating cell-free nucleic acids are isolated from the plasma fraction. The isolated cell-free nucleic acid sample includes a mixture of cfDNA and cfRNA.

In a step 115, first strand cDNA is synthesized from cfRNA in the cell-free nucleic acid sample. For example, random hexamer primers with a 3'-OH group and a high-fidelity reverse transcriptase are used to synthesize first strand cDNA in a reverse transcription reaction. The cell-free nucleic acid sample now includes a mixture of cfDNA and short cfRNA/cDNA hybrid molecules.

In a step 120, the cfRNA in the cfRNA/cDNA hybrid molecules is degraded using, for example, excess RNase H. The cell-free nucleic acid sample now includes a mixture of cfDNA and first strand cDNA fragments that have a hydroxyl group on the 3' end of the molecule.

In a step 125, a tag oligonucleotide (represented in the figure as a universal ligation adapter) is ligated onto the 3' end of the first strand cDNA using a single strand DNA ligase (e.g., adaptase from Swift Biosciences or Thermostable 5' AppDNA/RNA Ligase from New England BioLabs). The single strand DNA ligase is selected for specificity to single strand DNA (i.e., non-specific for double strand cfDNA in the cell-free nucleic acid sample). The universal ligation adapter includes, for example, a barcode sequence and a universal primer sequence. The universal ligation adapter may also include a unique molecular identifier (UMI) which can be used to reduce error introduced by amplification, library preparation, and sequencing. The cell-free nucleic acid sample now includes a mixture of cfDNA and single stranded cDNA (derived from cfRNA) that is tagged with a unique barcode.

In a step 130, second strand cDNA is synthesized. For example, second strand cDNA is synthesized in an extension reaction using the universal primer sequence on the universal ligation adapter as a primer. The cell-free nucleic acid sample now includes cfDNA and double stranded cDNA (derived from cfRNA) that is tagged with a unique barcode.

In a step 135, a sequencing library is prepared. For example, a sequencing library preparation protocol (e.g., TruSeq® library preparation protocol (Illumina, Inc.)) that includes the steps of end repair, 3' end A-tailing, sequencing adapter ligation, and PCR amplification is used to prepare a sequencing library. The sequencing library now includes amplicons from cfDNA and barcoded cDNA (derived from cfRNA).

In another example (not illustrated), an end repair reaction is used to repair any overhanging ends in the double stranded cfDNA population prior to step 115 (first strand cDNA synthesis) of method 100.

Figure 2A:
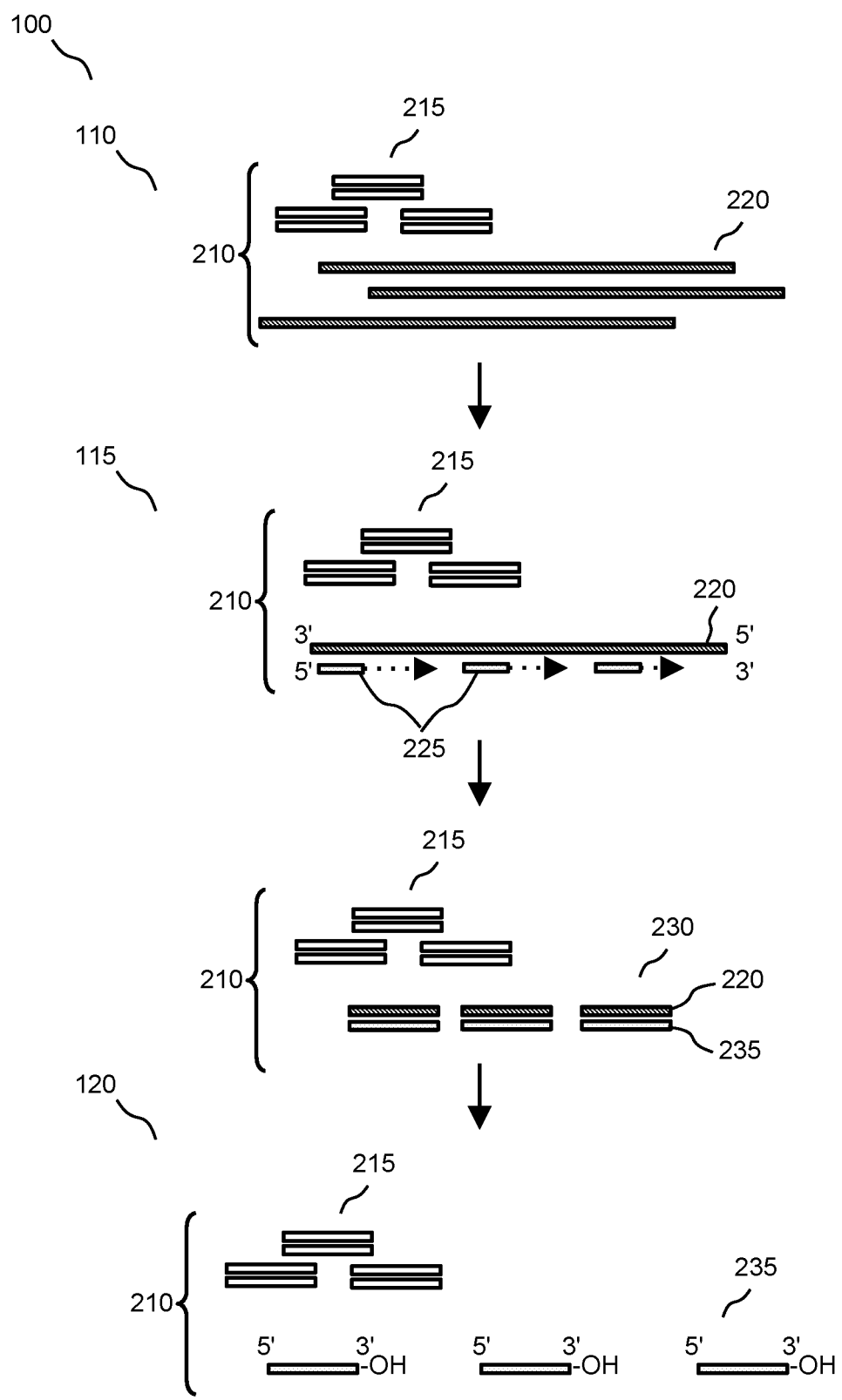
FIGS. 2A and 2B show pictorially example steps of a method in accordance with FIG. 1.
Figure 2B:
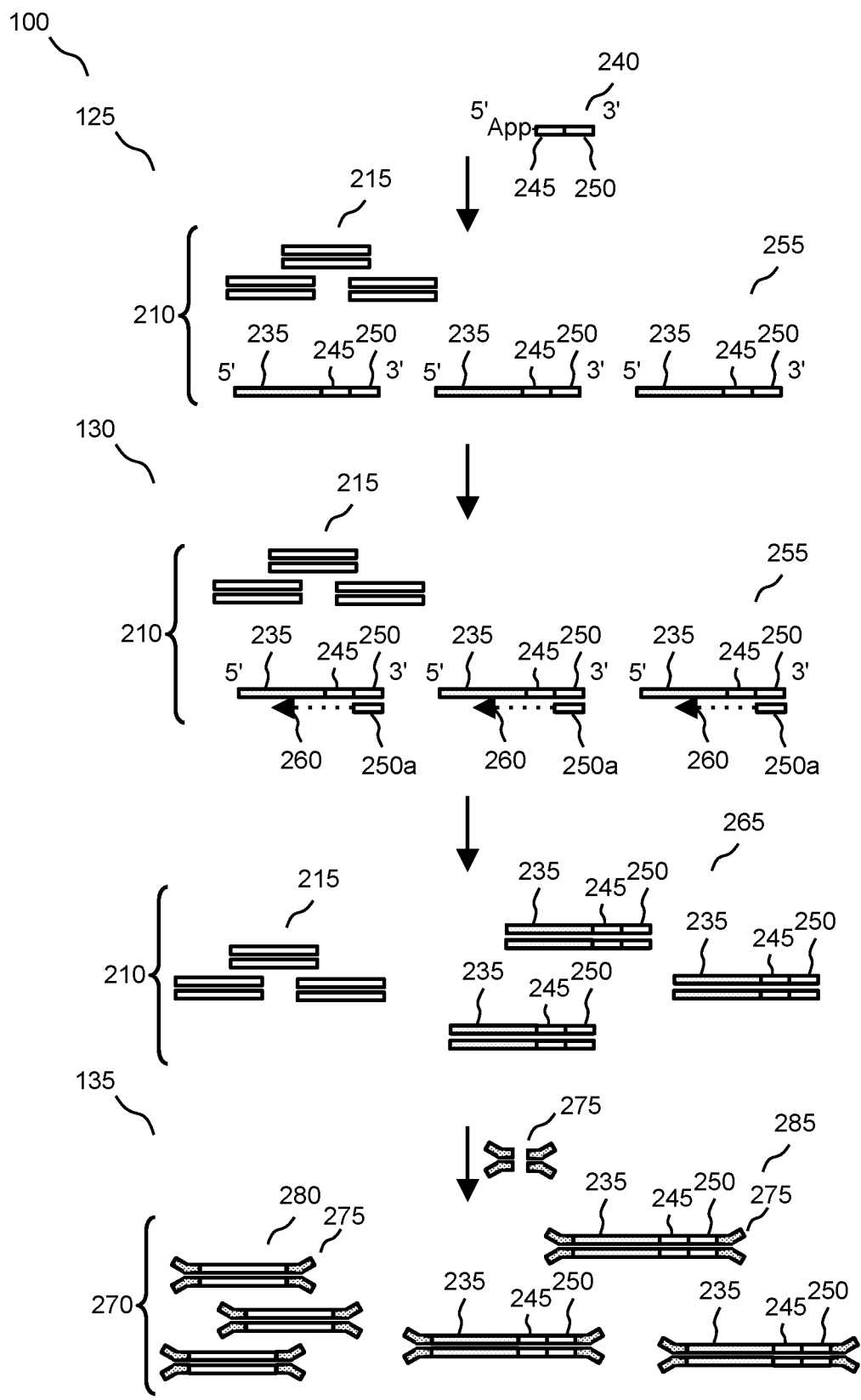

FIGS. 2A and 2B show pictorially the steps of method 100 of FIG. 1. Namely, at step 110, a blood sample is obtained and circulating cell-free nucleic acids are isolated from the plasma fraction (not illustrated). An isolated cell-free nucleic acid sample 210 includes a mixture of cfDNA 215 and cfRNA 220.

At step 115, a random hexamer primer 225 is used in a reverse transcription reaction to synthesize first strand cDNA 235 from cfRNA 220 in cell-free nucleic acid sample 210. The reverse transcriptase (not shown) used to transcribe cDNA from cfRNA in cell-free nucleic acid sample 210 is a high-fidelity reverse transcriptase. Cell-free nucleic acid sample 210 now includes a mixture of cfDNA 215 and short cfRNA/cDNA hybrid molecules 230. cfRNA/cDNA hybrid molecules 230 include a fragment of cfRNA 220 and a first strand cDNA molecule 235.

At step 120, cfRNA 220 in cfRNA/cDNA hybrid molecules 230 is degraded. In one example, cfRNA 220 is degraded using an excess of RNase H. Cell-free nucleic acid sample 210 now includes a mixture of cfDNA 215 and first strand cDNAs 235 (derived from cfRNA 220) that have a hydroxyl group on the 3' end of the molecule.

At step 125, a universal ligation adapter 240 is ligated onto the 3' end of first strand cDNAs 235. Universal ligation adapter 240 includes a 5' adenyl group, a barcode region 245, and a universal primer region 250. Universal ligation adapter 240 is ligated onto the 3'-OH end of first strand cDNAs 235 using a single strand DNA ligase to yield a population of tagged first strand cDNA molecules 255.

At step 130, a second strand cDNA 260 is synthesized. For example, second strand cDNA 260 is synthesized in an extension reaction using a primer 250a that is complementary to universal primer region 250. Cell-free nucleic acid sample 210 now includes a mixture of cfDNA 215 and a population of double stranded cDNA molecules 265 (derived from cfRNA 220) that are tagged with barcode region 245.

At step 135, a sequencing library 270 is prepared. For example, a sequencing library preparation protocol (e.g., TruSeq® library preparation protocol (Illumina, Inc.)) that includes the steps of end repair (not illustrated), 3' end A-tailing (not illustrated), ligation of sequencing adapters 275, and PCR amplification (not illustrated) is used to prepare sequencing library 270. Sequencing library 270 includes cfDNA amplicons 280 and cDNA amplicons 285 (derived from cfRNA 220). cDNA amplicons 285 include barcode region 245 and universal primer region 250.

Example 2

Figure 3:
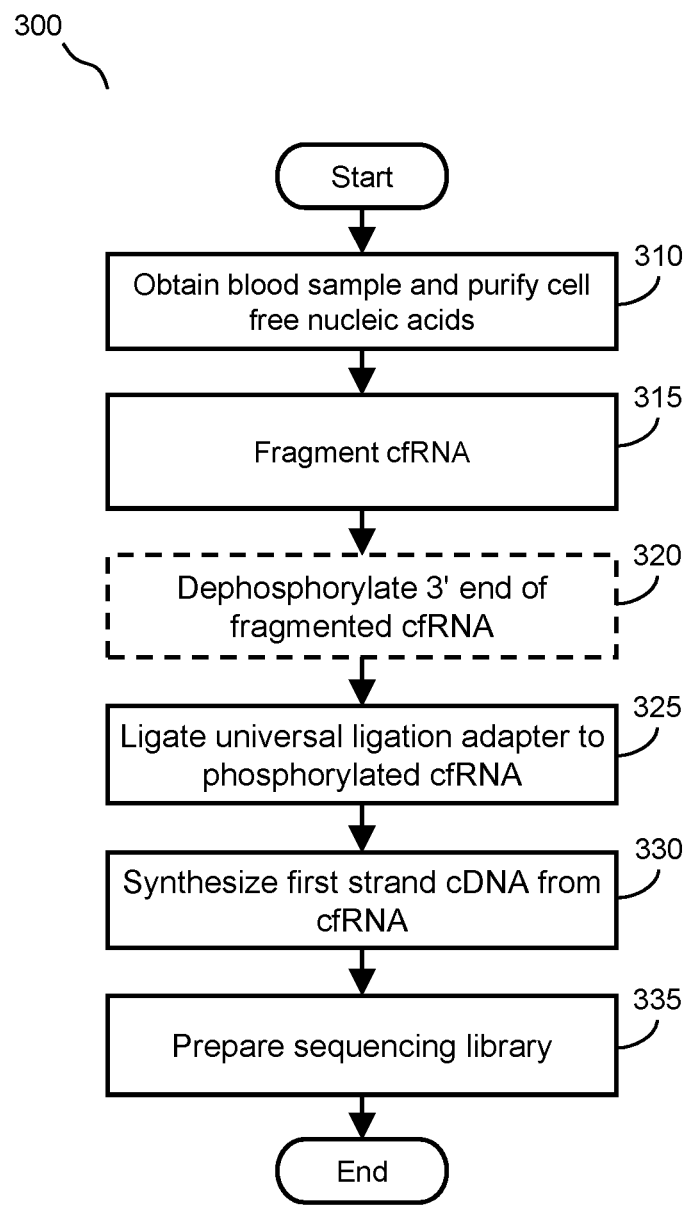
FIG. 3 illustrates a flow diagram of an example method of preparing a cell-free nucleic acid library using single strand RNA (ssRNA) ligation to tag cfRNA in a cell-free nucleic acid sample

FIG. 3 illustrates a flow diagram of an example of a method 300 of preparing a cell-free nucleic acid library using single strand RNA ligation to tag cfRNA in a cell-free nucleic acid sample. Method 300 includes, but is not limited to, the following steps.

In a step 310, a blood sample is obtained and circulating cell-free nucleic acids are isolated from the plasma fraction. The isolated cell-free nucleic acid sample includes a mixture of cfDNA and cfRNA.

In a step 315, cfRNA in the cell-free nucleic acid sample is fragmented to a certain size range. In one example, the cfRNA is fragmented using a physical fragmentation protocol (e.g., sonication). In another example, the cfRNA is fragmented using a chemical fragmentation protocol (e.g., alkaline digestion, or divalent metal cation (e.g., $Mg^{2+}$) and heat (e.g., about 94° C.)). Fragmentation reaction conditions are selected such that cfRNA in the cell-free nucleic acid sample is fragmented to a certain size range and cfDNA is not fragmented.

In an optional step 320, depending on the method used to fragment the cfRNA in step 315, the 3' ends of the fragmented cfRNA may be phosphorylated. The 3' ends of the fragmented cfRNA can be dephosphorylated using T4 polynucleotide kinase, thereby leaving a 3'-OH.

In a step 325, a tag oligonucleotide (represented in the figure as a universal ligation adapter) is ligated onto the 3' end of the cfRNA using an RNA ligase (e.g., T4 RNA ligase). The universal ligation adapter includes a barcode sequence and a universal primer sequence. The universal ligation adapter may also include a unique molecular identifier (UMI) which can be used to reduce errors introduced by amplification, library preparation, and sequencing. The cell-free nucleic acid sample now includes cfDNA and fragmented cfRNA that is tagged with a unique barcode and a universal primer sequence.

In a step 330, first strand cDNA is synthesized from adapter ligated cfRNA (cfRNA that is tagged with the unique barcode and the universal primer sequence). First strand cDNA can be synthesized from adapter ligated cfRNA using any reverse transcription reaction that uses the universal primer region in the universal ligation adapter as a primer. In one example, first strand cDNA is synthesized from cfRNA in a template switch reverse transcription reaction (e.g., Clontech) using the universal primer sequence in the universal ligation adapter as a primer.

In a step 335, a sequencing library is prepared. For example, a sequencing library preparation protocol (e.g., TruSeq® library preparation protocol (Illumina, Inc.)) that includes the steps of end repair, 3' end A-tailing, sequencing adapter ligation, and PCR amplification is used to prepare a sequencing library. The sequencing library now includes amplicons from cfDNA and barcoded cDNA (derived from cfRNA).

Figure 4A:
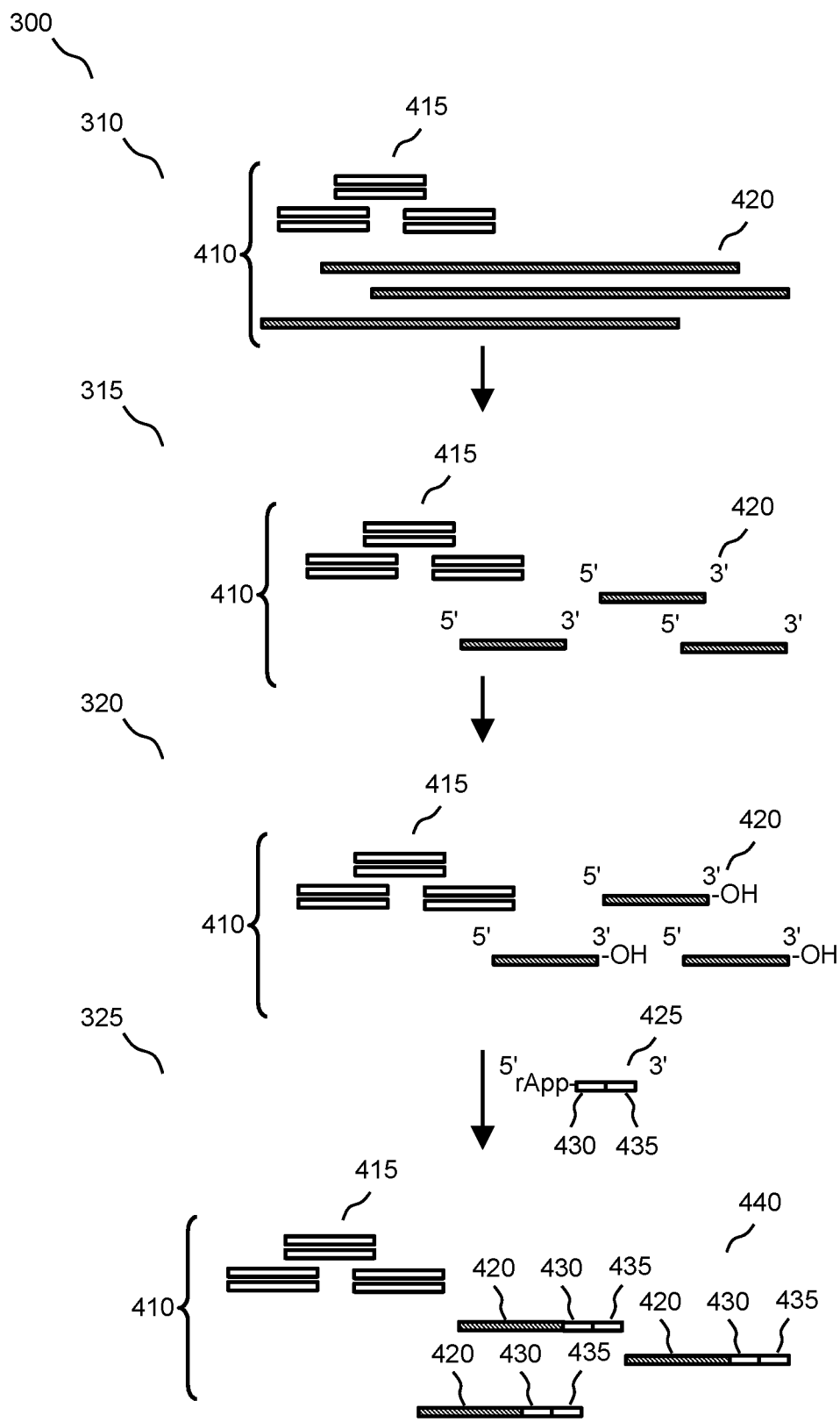
FIGS. 4A and 4B show pictorially example steps of a method in accordance with FIG. 3.
Figure 4B:
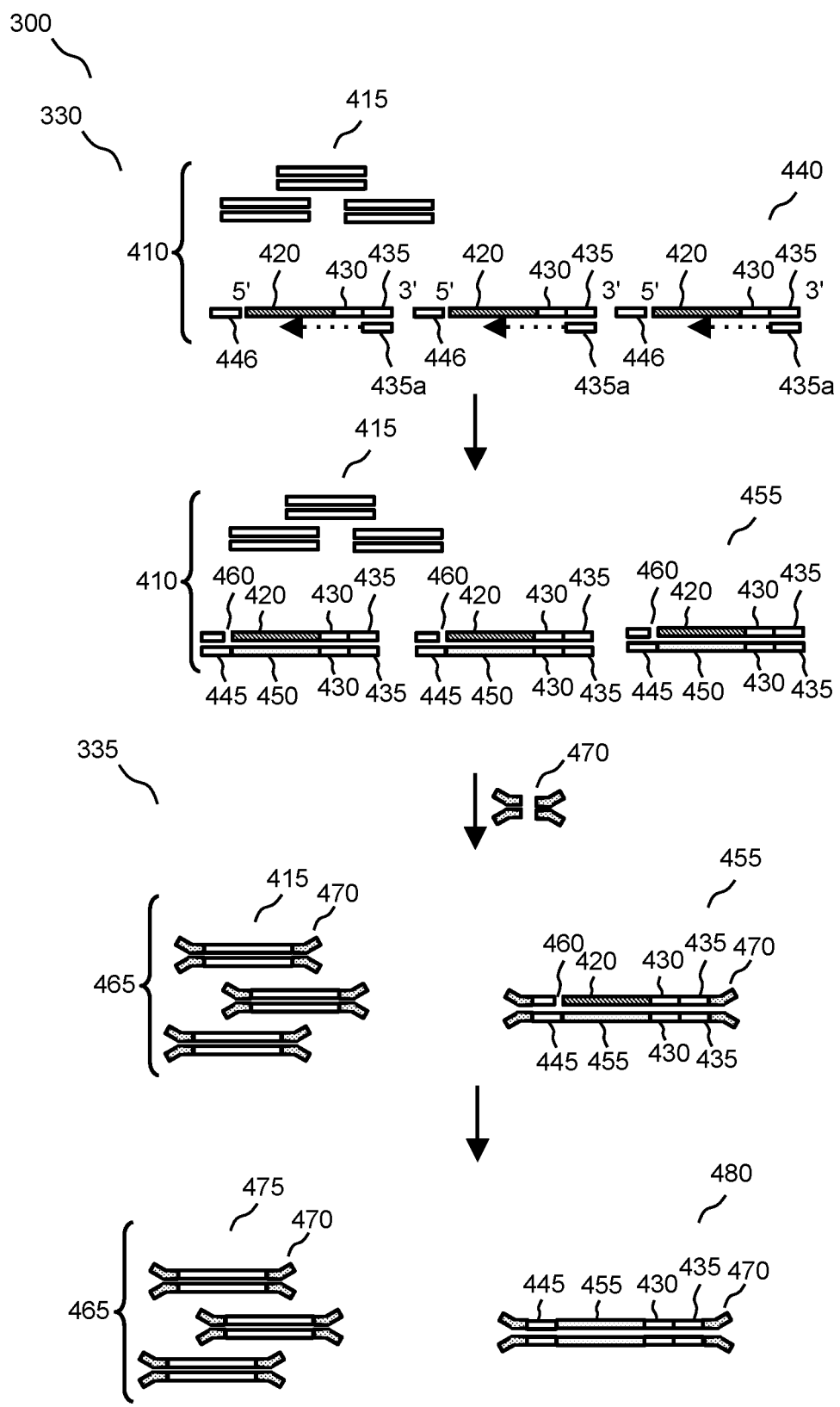

FIGS. 4A and 4B show pictorially the steps of method 300 of FIG. 3. Namely, in step 310, a blood sample is obtained and circulating cell-free nucleic acids are isolated from the plasma fraction (not illustrated). An isolated cell-free nucleic acid sample 410 includes a mixture of cfDNA 415 and cfRNA 420.

In step 315, cfRNA 420 in cell-free nucleic acid sample 410 is fragmented to a certain size range. In one example, cfRNA 420 is fragmented using an alkaline digestion protocol. The fragmentation reaction conditions are selected such that cfRNA 420 is fragmented to a certain size range and cfDNA 415 in cell-free nucleic acid sample 410 is not fragmented.

In optional step 320, the 3' ends of fragmented cfRNA 420 are dephosphorylated using T4 polynucleotide kinase.

In step 325, a universal ligation adapter 425 is ligated onto the 3' OH of cfRNA 420. Universal ligation adapter 425 includes a 5' adenyl group (rApp), a barcode region 430, and a universal primer region 435. Universal ligation adapter 425 is ligated onto the 3' end of cfRNA 420 using an RNA ligase (e.g., T4 RNA ligase) to yield a population of cfRNA molecules 440 that include barcode region 430 and universal primer region 435.

In step 330, a first strand cDNA 450 is synthesized from cfRNA 440 (cfRNA 420 that is tagged with unique barcode region 430 and universal primer region 435). In this example, first strand cDNA 450 is synthesized from cfRNA 440 in a template switch reverse transcription reaction using a primer 435a that is complementary to universal primer region 435 and a template switch oligonucleotide 446 (which when used as a template for continued primer extension adds a complement of at least a portion thereof 445) to yield a population of cfRNA/cDNA hybrid molecules 455. During the template switch reverse transcription reaction, a nick 460 is formed adjacent to cfRNA 420 in cfRNA/cDNA hybrid molecules 455.

In step 335, a sequencing library 465 is prepared. For example, a sequencing library preparation protocol (e.g., TruSeq® library preparation protocol (Illumina, Inc.)) that includes the steps of end repair (not illustrated), 3' end A-tailing (not illustrated), ligation of sequencing adapters 470, and PCR amplification is used to prepare sequencing library 465. Because of nick 460 in cfRNA/cDNA hybrid molecules 455, cfRNA strand 420 is not amplified during the PCR amplification step of the illustrated method. Sequencing library 465 includes cfDNA amplicons 475 and cDNA amplicons 480 (derived from cfRNA 420). cDNA amplicons 480 include barcode region 430 and universal primer region 435.

FIGS. 5A and 5B show a schematic diagram of other configurations of a universal ligation adapter 500 and a template switch oligonucleotide 525, respectively, that can be used in step 325 of FIG. 4A and step 330 of FIG. 4B, respectively. Referring to FIG. 5A, a universal ligation adapter 500 includes barcode region 430, universal primer region 435, a sequencing by synthesis (SBS) primer region 510, and a P7 primer region 515. Referring to FIG. 5B, a template switch oligonucleotide 525 includes universal switch primer 545, an SBS primer region 530, and a P5 primer region 535. Because universal ligation adapter 500 includes SBS region 510 and P7 primer region 515, and template switch oligonucleotide 525 includes SBS region 530 and P5 region 535, ligation of sequencing adapters (e.g., sequencing adapters 470) onto cfRNA/cDNA hybrid molecules 455 is not required. In this example, the ends of cfRNA/cDNA hybrid molecules 455 with universal ligation adapter 500 and template switch primer 525 thereon are then blocked and a separate ligation step is then used to add sequencing adapters onto cfDNA 415.

Example 3

Figure 6:
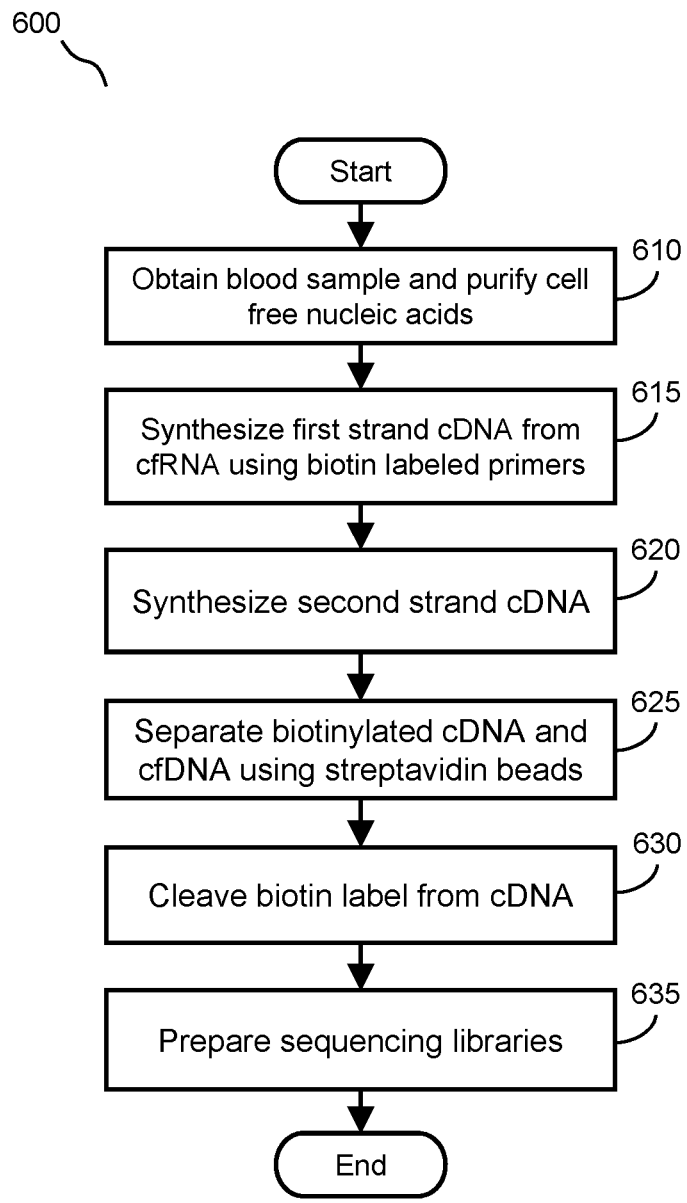
FIG. 6 illustrates a flow diagram of an example of a method of preparing cell-free nucleic acid libraries using biotin-labeled random hexamer primers to tag cDNA reverse transcribed from cfRNA in a cell-free nucleic acid sample.

FIG. 6 illustrates a flow diagram of an example of a method 600 of preparing cell-free nucleic acid libraries using biotin-labeled random hexamer primers to tag cDNA reverse transcribed from cfRNA in a cell-free nucleic acid sample. In this example, the biotin label incorporated into double stranded cDNA derived from cfRNA is used to separate the cell-free nucleic acid sample into a cfDNA fraction and a cDNA fraction (derived from cfRNA) for preparation of two separate sequencing libraries. Method 600 includes, but is not limited to, the following steps.

In a step 610, a blood sample is obtained and circulating cell-free nucleic acids are isolated from the plasma fraction. The isolated cell-free nucleic acid sample includes a mixture of cfDNA and cfRNA.

In a step 615, first strand cDNA is synthesized from cfRNA in the cell-free nucleic acid sample using biotin-labeled random hexamer primers, wherein the biotin label is attached to the random hexamer primers via a cleavable uracil residue. The biotin-labeled random hexamer primers may also include a unique molecular identifiers (UMIs) which can be used to reduce errors introduced by amplification, library preparation, and sequencing. The cell-free nucleic acid sample now includes a mixture of cfDNA and short biotinylated cfRNA/cDNA hybrid molecules.

In a step 620, second strand cDNA is synthesized using, for example, DNA polymerase and RNase H.

In a step 625, biotinylated cDNA is captured using streptavidin beads and the cell-free nucleic acid sample is split into a biotinylated cDNA pellet fraction (derived from cfRNA) and a cfDNA supernatant fraction.

In a step 630, the biotin label is cleaved off the double stranded cDNA using, for example, USER enzymes. USER enzyme is a mixture of uracil DNA glycosylase (UDG) and the DNA glycosylase-lyase endonuclease VIII. USER enzymes removes the uracil residue in the double stranded cDNA thereby releasing the biotin label from the double stranded cDNA.

In a step 635, two separate sequencing libraries are prepared. For example, a sequencing library preparation protocol (e.g., TruSeq® library preparation protocol (Illumina, Inc.)) that includes the steps of end repair, 3' end A-tailing, sequencing adapter ligation, and PCR amplification is used to prepare a cfDNA sequencing library. Similarly, a sequencing library preparation protocol (e.g., TruSeq® library preparation protocol (Illumina, Inc.)) that includes the steps of end repair, 3' end A-tailing, sequencing adapter ligation, and PCR amplification is used to prepare a cDNA sequencing library (derived from cfRNA).

Figure 7A:
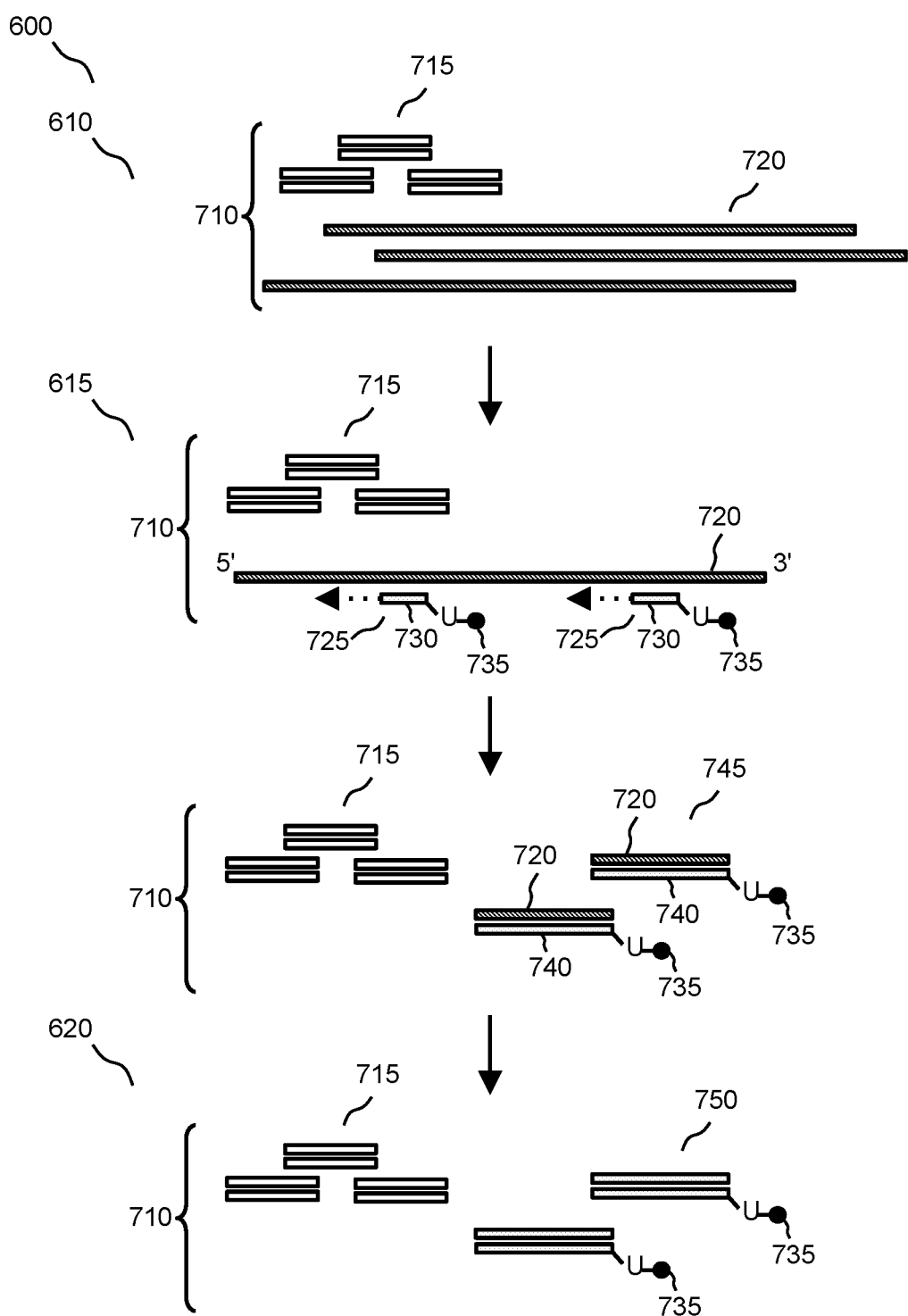
FIGS. 7A and 7B show pictorially example steps of a method in accordance with FIG. 6.
Figure 7B:
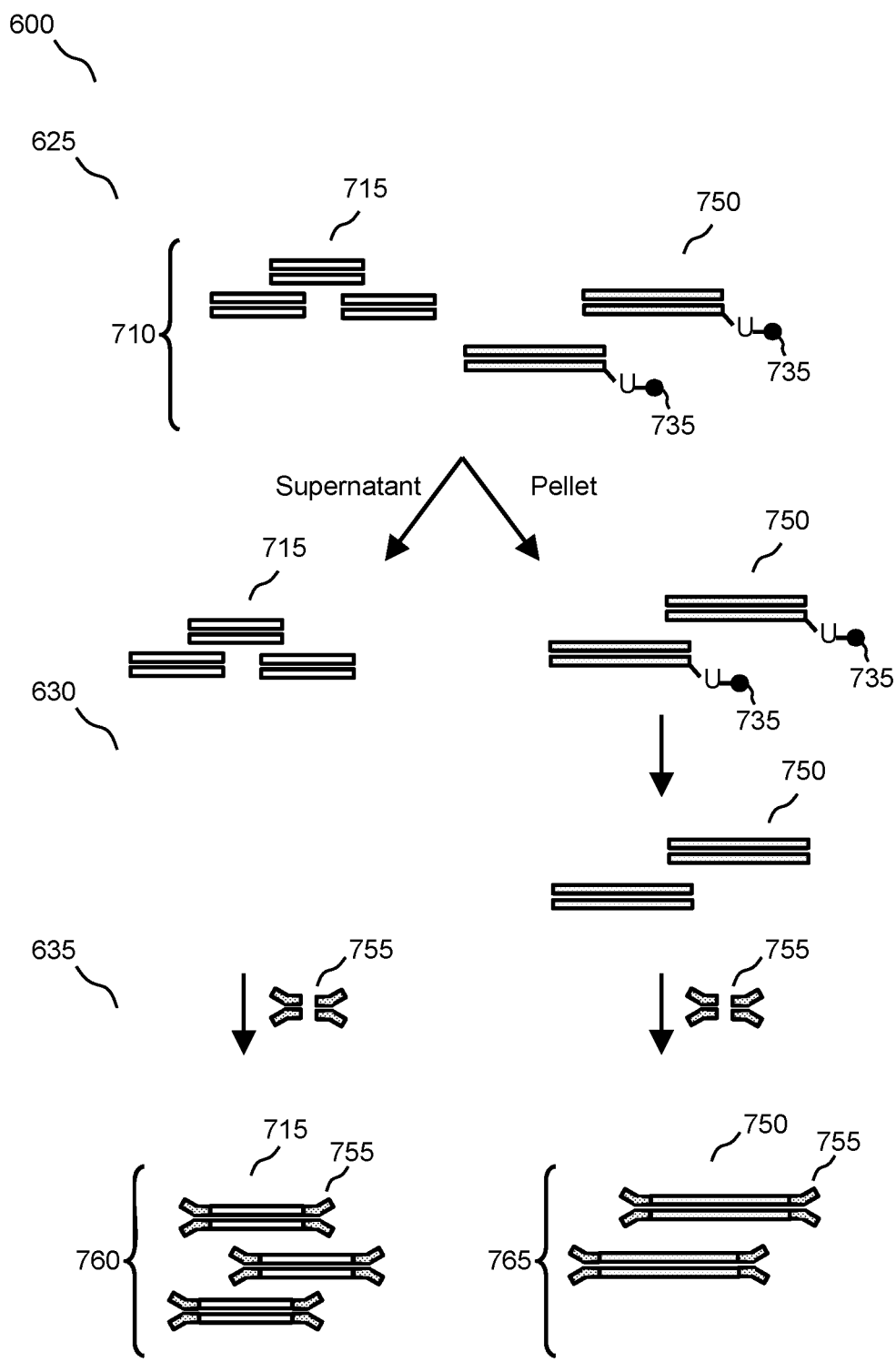

FIGS. 7A and 7B show pictorially the steps of method 600 of FIG. 6. Namely, in step 610, a blood sample is obtained and circulating cell-free nucleic acids are isolated from the plasma fraction (not illustrated). An isolated cell-free nucleic acid sample 710 includes a mixture of cfDNA 715 and cfRNA 720.

In step 615, a random hexamer primer 725 that includes a random primer sequence 730 and a biotin label 735 is used in a reverse transcription reaction to synthesize first strand cDNA 740 from cfRNA 720 in cell-free nucleic acid sample 710. Biotin label 735 is attached to random primer sequence 730 via a uracil residue (U). Cell-free nucleic acid sample 710 now includes a mixture of cfDNA 715 and short cfRNA/cDNA hybrid molecules 745 that include a fragment of cfRNA 720 and a cDNA molecule 740 that is tagged with biotin label 735.

In step 620, second strand cDNA is synthesized using, for example, DNA polymerase and RNase H. Cell-free nucleic acid sample 710 now includes a mixture of cfDNA 715 and double stranded cDNA 750 (derived from cfRNA 720) that is tagged with biotin label 735.

In step 625, double stranded cDNA 750 with biotin label 735 thereon is captured using streptavidin beads and cell-free nucleic acid sample 710 is split into a double stranded cDNA 750 pellet fraction and a cfDNA 715 supernatant fraction.

In step 630, biotin label 735 is cleaved off double stranded cDNA 750 using, for example, USER enzymes that remove the uracil residue (U) in double stranded cDNA 750 thereby releasing biotin label 735 from double stranded cDNA 750.

In step 635, two separate sequencing libraries are prepared. For example, a sequencing library preparation protocol (e.g., TruSeq® library preparation protocol (Illumina, Inc.)) that includes the steps of end repair (not illustrated), 3' end A-tailing (not illustrated), ligation of sequencing adapters 755, and PCR amplification (not illustrated) is used to prepare a cfDNA sequencing library 760. Similarly, a sequencing library preparation protocol that includes the steps of end repair (not illustrated), 3' end A-tailing (not illustrated), ligation of sequencing adapters 755, and PCR amplification (not illustrated) is used to prepare a cDNA sequencing library 765 (derived from cfRNA).

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

What is claimed is:

1. A method of distinguishing sequences of RNA and DNA from a biological sample, the method comprising:
   a. obtaining the sample comprising the RNA and the DNA;
   b. joining a tag oligonucleotide comprising a tag sequence to the RNA in a reaction comprising an RNA ligase to produce tagged RNA;
   c. reverse transcribing the tagged RNA to produce tagged cDNA; and
   d. sequencing the DNA and the tagged cDNA;
   wherein the joining, reverse transcribing, and sequencing are performed in the presence of the DNA.

2. The method of claim 1, wherein the RNA and DNA are cell-free nucleic acids.

3. The method of claim 1, further comprising fragmenting the RNA to produce fragmented RNA prior to joining the tag sequence.

4. The method of claim 3, wherein the fragmented RNA have an average size within a pre-defined range.

5. The method of claim 2, wherein (i) the tag oligonucleotide is joined to a 3' end of the RNA; and (ii) the tag oligonucleotide comprises a primer binding sequence.

6. The method of claim 5, wherein the reverse transcribing comprises extending a primer hybridized to the primer binding sequence.

7. The method of claim 1, wherein (i) the reverse transcribing comprises extension of a tagged cDNA along a template switch oligonucleotide (TSO); and (ii) the TSO comprises a universal switch primer sequence.

8. The method of claim 1, further comprising using a processor to group RNA-derived sequences separately from DNA-derived sequences based on the presence or absence of the tag sequence, or a complement of the tag sequence.

9. The method of claim 8, further comprising identifying presence or absence of a condition of a subject based on the RNA-derived sequences and the DNA-derived sequences.

10. The method of claim 9, wherein (i) the condition is cancer; or (ii) the method further comprises treating the subject based on the RNA-derived sequences and the DNA-derived sequences.

11. The method of claim 1, wherein the tag oligonucleotide is joined to a 3' end of the RNA.

12. The method of claim 1, wherein the reverse transcribing comprises extension of the tagged cDNA along a template-switch oligonucleotide (TSO).

13. The method of claim 1, wherein the sequencing comprises amplifying the tagued cDNA to produce double-stranded tagged cDNA.

14. The method of claim 1, wherein the sequencing comprises joining sequencing adapters to the tagged cDNA and the DNA.

15. The method of claim 1, wherein the tag oligonucleotide comprises a unique molecular identifier (UMI), wherein each of a plurality of tagged cDNA molecules is distinguishable from others in the plurality of tagged cDNA molecules based on the UMI.

16. The method of claim 1, wherein the sample is blood, a blood fraction, plasma, serum, saliva, sputum, urine, semen, transvaginal fluid, cerebrospinal fluid, or stool.

17. The method of claim l, wherein the reverse transcribing comprises extension of primers comprising a random sequence.

18. The method of claim 3, wherein fragmenting the RNA comprises subjecting the RNA and DNA to conditions that preferentially fragment the RNA.

19. The method of claim 3, wherein fragmenting the RNA comprises sonication, chemical fragmentation, or heating.

20. The method of claim 3, wherein the method further comprises dephosphorylating 3' ends of fragmented RNA.

* * * * *

UNITED STATES PATENT AND TRADEMARK OFFICE
CERTIFICATE OF CORRECTION

| | |
|---|---|
| PATENT NO. | : 11,180,801 B2 |
| APPLICATION NO. | : 16/177105 |
| DATED | : November 23, 2021 |
| INVENTOR(S) | : Matthew Larson et al. |

It is certified that error appears in the above-identified patent and that said Letters Patent is hereby corrected as shown below:

In the Claims

Column 42, Line 14, in the second line of Claim 13, delete "tagued cDNA" and insert --tagged cDNA--

Signed and Sealed this
Third Day of January, 2023

Katherine Kelly Vidal
*Director of the United States Patent and Trademark Office*